United States Patent
Stahmann et al.

(10) Patent No.: US 9,724,522 B2
(45) Date of Patent: Aug. 8, 2017

(54) MEDICAL DEVICE SYSTEMS AND METHODS WITH MULTIPLE COMMUNICATION MODES

(71) Applicant: Cardiac Pacemakers, Inc., St. Paul, MN (US)

(72) Inventors: Jeffrey E. Stahmann, Ramsey, MN (US); Keith R. Maile, New Brighton, MN (US); Brendan E. Koop, Ham Lake, MN (US); Michael J. Kane, St. Paul, MN (US); Jacob M. Ludwig, Isanti, MN (US); Paul Huelskamp, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/398,355

(22) Filed: Jan. 4, 2017

(65) Prior Publication Data

US 2017/0136248 A1 May 18, 2017

Related U.S. Application Data

(63) Continuation of application No. 14/813,054, filed on Jul. 29, 2015, now Pat. No. 9,572,991.

(60) Provisional application No. 62/034,494, filed on Aug. 7, 2014.

(51) Int. Cl.
*A61N 1/37* (2006.01)
*A61N 1/372* (2006.01)
*A61N 1/375* (2006.01)

(52) U.S. Cl.
CPC ......... *A61N 1/37288* (2013.01); *A61N 1/371* (2013.01); *A61N 1/3727* (2013.01); *A61N 1/3756* (2013.01)

(58) Field of Classification Search
None
See application file for complete search history.

(56) References Cited

U.S. PATENT DOCUMENTS

| | | | |
|---|---|---|---|
| 6,400,990 | B1 | 6/2002 | Silvian |
| 7,110,824 | B2 | 9/2006 | Amundson et al. |
| 8,509,910 | B2 | 8/2013 | Sowder et al. |
| 8,571,678 | B2 | 10/2013 | Wang |
| 8,744,572 | B1 | 6/2014 | Greenhut et al. |
| 2007/0088405 | A1 | 4/2007 | Jacobson |
| 2012/0109236 | A1 | 5/2012 | Jacobson et al. |
| 2013/0041422 | A1 | 2/2013 | Jacobson |
| 2013/0231710 | A1 | 9/2013 | Jacobson |
| 2014/0214104 | A1 | 7/2014 | Greenhut et al. |

FOREIGN PATENT DOCUMENTS

WO 2013080038 A2 6/2013

*Primary Examiner* — Ankit D Tejani
(74) *Attorney, Agent, or Firm* — Seager, Tufte & Wickhem LLP.

(57) ABSTRACT

Medical device systems and methods with multiple communication modes. An example medical device system may include a first medical device and a second medical device communicatively coupled to the first medical device. The first medical device may be configured to communicate information to the second medical device in a first communication mode. The first medical device may further be configured to communicate information to the second medical device in a second communication mode after determining that one or more of the communication pulses captured the heart of the patient.

20 Claims, 16 Drawing Sheets

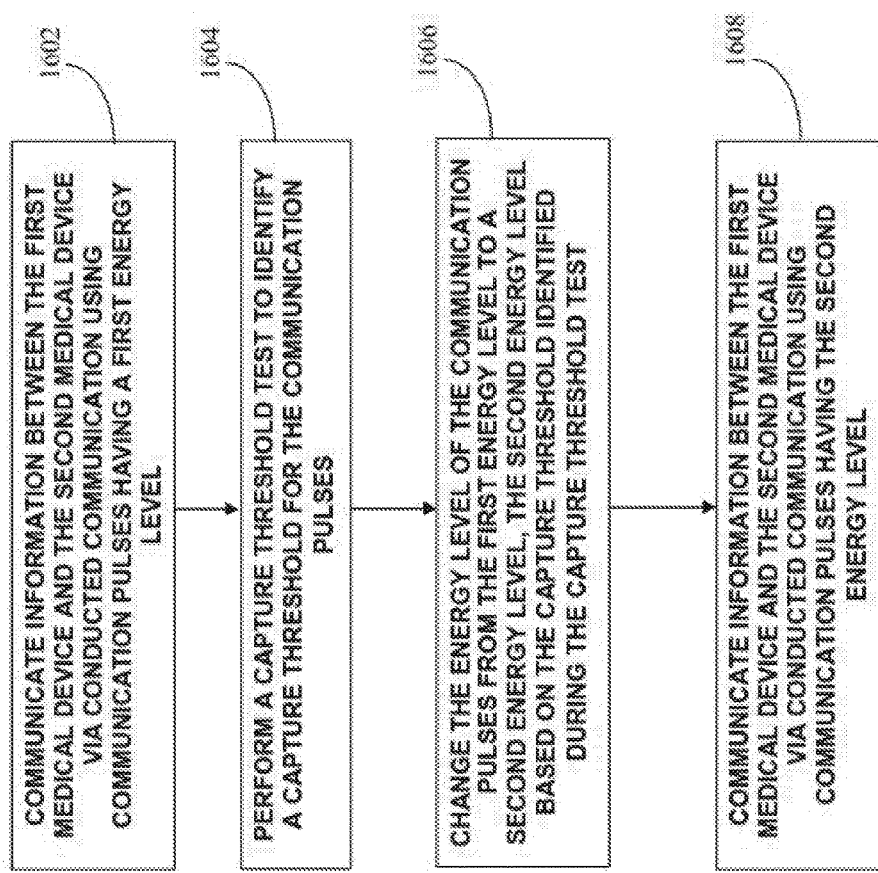

MEDICAL DEVICE SYSTEMS AND METHODS WITH MULTIPLE COMMUNICATION MODES

CROSS-REFERENCE TO RELATED APPLICATIONS

This application is a continuation of co-pending U.S. patent application Ser. No. 14/813,054, filed on Jul. 29, 2015, which claims priority under 35 U.S.C. §119 to U.S. Provisional Application Ser. No. 62/034,494, filed on Aug. 7, 2014, both of which are incorporated herein by reference.

TECHNICAL FIELD

The present disclosure generally relates to systems, devices, and methods for communicating information, and more particularly, to systems, devices, and methods for communicating information between medical devices.

BACKGROUND

Implantable medical devices are commonly used today to monitor a patient and/or deliver therapy to a patient. For example, implantable sensors are often used to monitor one or more physiological parameters of a patient, such as heart beats, heart sounds, ECG, respiration, etc. In another example, implantable neurostimulators can be used to provide neurostimulation therapy to a patient. In yet another example, pacing devices can be used to treat patients suffering from various heart conditions that may result in a reduced ability of the heart to deliver sufficient amounts of blood to a patient's body. Such heart conditions may lead to rapid, irregular, and/or inefficient heart contractions. To help alleviate some of these conditions, various devices (e.g., pacemakers, defibrillators, etc.) are often implanted in a patient's body. Such devices may monitor and provide electrical stimulation to the heart to help the heart operate in a more normal, efficient and/or safe manner. Regardless of the type of device, it is often desirable for the implantable medical device to communicate with another medical device.

SUMMARY

The present disclosure generally relates to systems, devices, and methods for communicating information, and more particularly, to systems, devices, and methods for communicating information between medical devices. In some instances, communication signals used for communication between medical devices may cause an undesirable effect in the patient. For example, the communication signals may be communication pulses that capture the heart. In some example, when this occurs, the communication may be switched from a first communication mode to a second communication mode. In some cases, the second communication mode is less likely to cause the undesirable effect in the patient.

In one example, a medical device system may include: a first medical device; and a second medical device communicatively coupled to the first medical device, the first medical device is configured to communicate information to the second medical device in a first communication mode, and the first medical device is configured to communicate information to the second medical device in a second communication mode after determining that one or more of the communication pulses captured the heart of the patient.

Alternatively, or additionally, in any of the above examples wherein: in the first communication mode, the first medical device may be configured to communicate information to the second medical device only during a first period of time following a detected cardiac event; in the second communication mode, the first medical device may be configured to communicate information to the second medical device only during a second period of time following a detected cardiac event; and wherein the second period of time is shorter than the first period of time.

Alternatively, or additionally, in any of the above examples, the detected cardiac event includes a heartbeat, and wherein the first period of time begins after the detected heartbeat and concludes before a subsequent heartbeat.

Alternatively, or additionally, in any of the above examples, the detected cardiac event includes a heartbeat, and wherein the second period of time begins after the detected heartbeat and concludes before a subsequent heartbeat.

Alternatively, or additionally, in any of the above examples, the detected cardiac event includes a heartbeat, and wherein the second period of time begins after a R wave of the detected heartbeat and concludes before a T wave of the detected heartbeat.

Alternatively, or additionally, in any of the above examples, the second period of time begins after a predetermined time delay after the detected cardiac event.

Alternatively, or additionally, in any of the above examples, the detected cardiac event includes a heartbeat, and wherein the first period of time begins after a refractory period of the detected heartbeat.

Alternatively, or additionally, in any of the above examples, the detected cardiac event includes a heartbeat, and wherein the second period of time begins after a refractory period of the detected heartbeat.

Alternatively, or additionally, in any of the above examples, the detected cardiac event includes a heartbeat, and wherein the second period of time occurs during a refractory period of the detected heartbeat.

Alternatively, or additionally, in any of the above examples, the detected cardiac event includes a heartbeat, and wherein the second period of time comprises a period of time of about one hundred fifty milliseconds beginning after the detected heartbeat.

Alternatively, or additionally, in any of the above examples, to determine that one or more of the communication pulses captured the heart of the patient, the first medical device is configured to: determine a heartbeat rate; detect a heartbeat; determine a time when a subsequent heartbeat should occur based on a timing of the detected heartbeat and the determined heartbeat rate; communicate information to the second medical device in the first communication mode between; and determine if a subsequent heartbeat occurs within an event window that overlaps the determined time that the subsequent heartbeat should occur, and if so, determine that the conducted communication does not capture the heart, and if not, determine that the conducted communication does capture the heart.

Alternatively, or additionally, in any of the above examples, to determine that one or more of the communication pulses captured the heart of the patient, the first medical device is configured to: detect a heartbeat; communicate information to the second medical device in the first communication mode; and determine if a subsequent heartbeat occurs within an event window that is initiated a predetermined time delay after the first communication window, and if so, determine that the conducted communication captures the heart, and if not, determine that the conducted communication does not capture the heart.

Alternatively, or additionally, in any of the above examples, to determine that one or more of the communication pulses captured the heart of the patient, the first medical device is configured to perform a capture threshold test, wherein the capture threshold test comprises: delivering one or more communication pulses at a capture threshold energy level; determining if the one or more communication pulses at the capture threshold energy level captured the heart, and: if so, identifying a capture threshold based, at least in part, on the capture threshold energy level; and if not, changing the capture threshold energy level and returning the delivering step.

Alternatively, or additionally, in any of the above examples, changing the capture threshold energy level comprises increasing the capture threshold energy level.

Alternatively, or additionally, in any of the above examples, changing the capture threshold energy level comprises decreasing the capture threshold energy level.

In another example, a method of communicating information between a plurality of medical devices in a medical device system comprises: communicating information between a first medical device and a second medical device via conducted communication during each of a plurality of first communication windows; determining whether the conducted communication during one or more of the first communication windows captures a heart of a patient; and if it is determined that the conducted communication during one or more of the first communication windows captured the heart of the patient, communicating information between the first medical device and the second medical device via conducted communication during each of a plurality of second communication windows, wherein the second communication windows are shorter than the first communication windows.

Alternatively, or additionally, in any of the above examples, each of the first communication windows occurs between two successive heartbeats of the patient.

Alternatively, or additionally, in any of the above examples, each of the second communication windows occurs between two successive heartbeats of the patient.

Alternatively, or additionally, in any of the above examples, each of the second communication windows occurs between an R wave and a T wave of a heartbeat of the patient.

Alternatively, or additionally, any of the above examples may further comprise: detecting heartbeats of the patient; and wherein each of the plurality of first communication windows begins after a first predetermined time delay after a detected heartbeat.

Alternatively, or additionally, in any of the above examples, each of the plurality of second communication windows begins after a second predetermined time delay after a detected heartbeat.

Alternatively, or additionally, in any of the above examples, the first predetermined time delay results in each of the plurality of first communication windows beginning outside of a refractory period of the patient's heart.

Alternatively, or additionally, in any of the above examples, the second predetermined time delay results in each of the plurality of second communication windows beginning outside of a refractory period of the patient's heart.

Alternatively, or additionally, in any of the above examples, the second predetermined time delay results in each of the plurality of second communication windows beginning during a refractory period of the patient's heart.

Alternatively, or additionally, in any of the above examples, determining whether the conducted communication during one or more of the first communication windows captures the heart of the patient comprises: determining a heartbeat rate; detecting a heartbeat; determining a time when a subsequent heartbeat should occur based on a timing of the detected heartbeat and the determined heartbeat rate; communicating information between the first medical device and the second medical device via conducted communication during a first communication window that falls between the detected heartbeat and the determined time that the subsequent heartbeat should occur; and determining if a subsequent heartbeat occurs within an event window that overlaps the determined time that the subsequent heartbeat should occur, and if so, determining that the conducted communication does not capture the heart, and if not, determining that the conducted communication does capture the heart.

Alternatively, or additionally, in any of the above examples, determining whether the conducted communication during one or more of the first communication windows captures the heart of the patient comprises: detecting a heartbeat; communicating information between the first medical device and the second medical device via conducted communication during a first communication window that falls between the detected heartbeat and a subsequent heartbeat; and determining if a subsequent heartbeat occurs within an event window that is initiated a predetermined time delay after the first communication window, and if so, determining that the conducted communication captures the heart, and if not, determining that the conducted communication does not capture the heart.

In yet another example, a method of communicating information between a plurality of medical devices in a medical device system, wherein at least one of the medical devices is an implantable medical device for implantation in a patient, comprises: communicating information between the first medical device and the second medical device via conducted communication using communication pulses having a first energy level; performing a capture threshold test to identify a capture threshold for the communication pulses; changing the energy level of the communication pulses from the first energy level to a second energy level, the second energy level based on the capture threshold identified during the capture threshold test; and communicating information between the first medical device and the second medical device via conducted communication using communication pulses having the second energy level.

Alternatively, or additionally, in any of the above examples, the first energy level is represented by a first pulse amplitude and a first pulse width, and the second energy level is represented by the first pulse amplitude and a second pulse width, wherein the second pulse width is different from the first pulse width.

Alternatively, or additionally, in any of the above examples, the first energy level is represented by a first pulse amplitude and a first pulse width, and the second energy level is represented by a second pulse amplitude and the first pulse width, wherein the second pulse amplitude is different from the first pulse amplitude.

Alternatively, or additionally, in any of the above examples, the first energy level is represented by a first pulse amplitude and a first pulse width, and the second energy level is represented by a second pulse amplitude and a second first pulse width, wherein the second pulse width is different from the first pulse width and the second pulse amplitude is different from the first pulse amplitude.

Alternatively, or additionally, in any of the above examples, performing the capture threshold test comprises: delivering one or more communication pulses at a capture threshold energy level; determining if the one or more communication pulses at the capture threshold energy level captured the heart, and: if so, identifying a capture threshold based, at least in part, on the capture threshold energy level; and if not, changing the capture threshold energy level and returning the delivering step.

Alternatively, or additionally, in any of the above examples, changing the capture threshold energy level comprises increasing the capture threshold energy level.

Alternatively, or additionally, in any of the above examples, changing the capture threshold energy level comprises decreasing the capture threshold energy level.

In still another example, a medical device system comprises: a first medical device; and a second medical device communicatively coupled to the first medical device, the first medical device is configured to communicate information to the second medical device in a first communication mode, and the first medical device is configured to communicate information to the second medical device in a second communication mode after determining that one or more of the communication pulses captured the heart of the patient.

Alternatively, or additionally, in any of the above examples, in the first communication mode, the first medical device is configured to communicate information to the second medical device only during a first period of time following a detected cardiac event; in the second communication mode, the first medical device is configured to communicate information to the second medical device only during a second period of time following a detected cardiac event; and wherein the second period of time is shorter than the first period of time.

Alternatively, or additionally, in any of the above examples, the detected cardiac event includes a heartbeat, and wherein the first period of time begins after the detected heartbeat and concludes before a subsequent heartbeat.

Alternatively, or additionally, in any of the above examples, the detected cardiac event includes a heartbeat, and wherein the second period of time begins after the detected heartbeat and concludes before a subsequent heartbeat.

Alternatively, or additionally, in any of the above examples, the detected cardiac event includes a heartbeat, and wherein the second period of time begins after a R wave of the detected heartbeat and concludes before a T wave of the detected heartbeat.

In another example, a medical device system for delivering electrical stimulation to a heart of a patient comprises: a first medical device configured to deliver pacing pulses to the heart of the patient; a second medical device communicatively coupled to the first medical device; wherein the second medical device is configured to deliver communication signals to tissue of the patient within a first predetermined time period after a detected cardiac event; and wherein, after determining that one or more delivered communication signals captured the heart of the patient, the second medical device is configured to deliver communication signals to tissue of the patient within a second predetermined time period after a detected cardiac event.

Alternatively, or additionally, in any of the above examples, to determine that one or more delivered communication signals captured the heart of the patient, the second medical device is configured to, after a first detected cardiac event, deliver one or more communication signals to the tissue of the patient a predetermined amount of time after the first detected cardiac event and determine whether a second detected cardiac event occurs within a detection window after the delivered one or more communication signals.

Alternatively, or additionally, in any of the above examples, the second medical device determines that one or more delivered communication signals captured the heart of the patient if the second medical device determines that the second detected cardiac event occurred within the detection window.

Alternatively, or additionally, in any of the above examples, the first detected cardiac event is a paced cardiac event.

Alternatively, or additionally, in any of the above examples, the first predetermined time period comprises the time between the detected cardiac event and a next detected cardiac event.

Alternatively, or additionally, in any of the above examples, the second predetermined time period comprises a time period of about one hundred fifty milliseconds beginning after the detected cardiac event.

In still another example, a medical device system may comprise a first medical device; and a second medical device communicatively coupled to the first medical device; the first medical device is configured to communicate information to the second medical device in a first communication mode using one or more communication pulses; and the first medical device is configured to communicate information to the second medical device in a second communication mode based on a determination of whether a communication pulse captured the heart.

Alternatively, or additionally, in any of the above examples, the first medical device is configured to communicate information to the second medical device in the second communication mode based on a determination that a communication pulse captured the heart.

Alternatively, or additionally, in any of the above examples, the first medical device is configured to communicate information to the second medical device in the second communication mode based on a determination that a communication pulse did not capture the heart.

Alternatively, or additionally, in any of the above examples, in the first communication mode, the first medical device is configured to communicate information to the second medical device only during a first period of time following a detected cardiac event; in the second communication mode, the first medical device is configured to communicate information to the second medical device only during a second period of time following a detected cardiac event; and wherein the second period of time is shorter than the first period of time.

Alternatively, or additionally, in any of the above examples, in the first communication mode, the first medical device is configured to communicate information to the second medical device only during a first period of time following a detected cardiac event; in the second communication mode, the first medical device is configured to communicate information to the second medical device only during a second period of time following a detected cardiac event; and wherein the second period of time is longer than the first period of time.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 16 is a flow diagram of an illustrative method that may be implemented by a medical device or medical device system, such as the illustrative medical devices and medical device systems described with respect to FIGS. 1-5.

Figure 1:
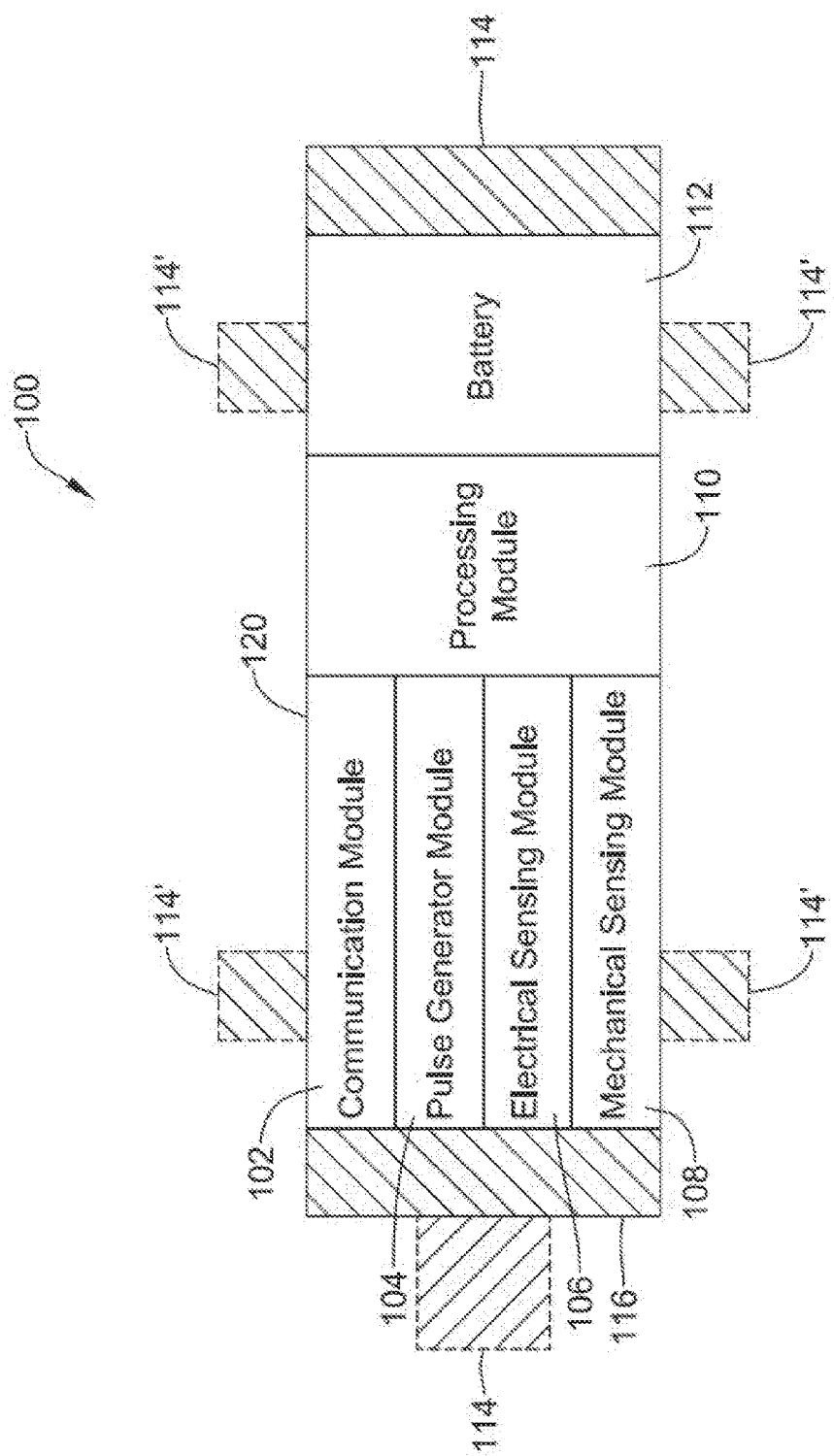
FIG. 1 is a schematic block diagram of an illustrative leadless cardiac pacemaker (LCP) according to one example of the present disclosure.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

A normal, healthy heart induces contraction by conducting intrinsically generated electrical signals throughout the heart. These intrinsic signals cause the muscle cells or tissue of the heart to contract. This contraction forces blood out of and into the heart, providing circulation of the blood throughout the rest of the body. However, many patients suffer from cardiac conditions that affect this contractility of their hearts. For example, some hearts may develop diseased tissues that no longer generate or conduct intrinsic electrical signals. In some examples, diseased cardiac tissues conduct electrical signals at differing rates, thereby causing an unsynchronized and inefficient contraction of the heart. In other examples, a heart may generate intrinsic signals at such a low rate that the heart rate becomes dangerously low. In still other examples, a heart may generate electrical signals at an unusually high rate. In some cases such an abnormality can develop into a fibrillation state, where the contraction of the patient's heart chambers are almost completely de-synchronized and the heart pumps very little to no blood. Implantable medical device which may be configured to determine occurrences of such cardiac abnormalities or arrhythmias and deliver one or more types of electrical stimulation therapy to patient's hearts may help to terminate or alleviate such cardiac conditions.

FIG. 1 depicts an exemplary leadless cardiac pacemaker (LCP) that may be implanted into a patient and may operate to prevent, control, or terminate cardiac arrhythmias in patients, for example by appropriately employing one or more therapies, such as electrical stimulation therapies (e.g. anti-tachycardia pacing (ATP) therapy, cardiac resynchronization therapy (CRT), bradycardia therapy, defibrillation pulses, or the like). As can be seen in FIG. 1, LCP 100 may be a compact device with all components housed within LCP 100 or directly on housing 120. As illustrated in FIG. 1, LCP 100 may include communication module 102, pulse generator module 104, electrical sensing module 106, mechanical sensing module 108, processing module 110, battery 112, and electrodes 114.

Communication module 102 may be configured to communicate with devices such as sensors, other medical devices, or the like, that are located externally to LCP 100. Such devices may be located either external or internal to the patient's body. Irrespective of the location, external devices (i.e. external to the LCP 100 but not necessarily external to the patient's body) can communicate with LCP 100 via communication module 102 to accomplish one or more desired functions. For example, LCP 100 may communicate information, such as sensed electrical signals, instructions, other messages, or data to an external medical device through communication module 102. The external medical device may use the communicated data and/or messages to perform various functions, such as determining occurrences of arrhythmias, delivering electrical stimulation therapy, storing received data, or other functions. LCP 100 may additionally receive data and/or other messages from the external medical device through communication module 102, and LCP 100 may use the received data and/or messages to perform various functions, such as determining occurrences of arrhythmias, delivering electrical stimulation therapy, storing received data, or other functions. Communication module 102 may be configured to use one or more methods for communicating with external devices. For example, communication module 102 may communicate via radiofrequency (RF) signals, inductive coupling, optical signals, acoustic signals, conducted communication signals, or any other signals suitable for communication. Communication techniques between LCP 100 and other devices will be discussed in further detail with reference to other Figures.

In the example shown in FIG. 1, pulse generator module 104 may be electrically connected to electrodes 114. In some examples, LCP 100 may additionally include electrodes 114'. In such examples, pulse generator 104 may additionally be electrically connected to electrodes 114'. Pulse generator module 104 may be configured to generate electrical stimulation signals. For example, pulse generator module 104 may generate electrical stimulation signals by using energy stored in battery 112 within LCP 100 and deliver the generated electrical stimulation signals via electrodes 114 and/or 114'. In at least some examples, pulse generator 104 of LCP 100 may further include switching circuitry to selectively connect one or more of electrodes 114 and/or 114' to pulse generator 104 in order to select via which electrodes 114/114' (and/or other electrodes) pulse generator 104 delivers the electrical stimulation therapy. Pulse generator module 104 may generate electrical stimulation signals with particular features or in particular sequences in order to provide one or multiple of a number of different stimulation therapies. For example, pulse generator module 104 may be configured to generate electrical stimulation signals to provide electrical stimulation therapy to combat bradycardia, tachycardia, cardiac synchronization, bradycardia arrhythmias, tachycardia arrhythmias, fibrillation arrhythmias, cardiac synchronization arrhythmias and/or any other suitable electrical stimulation therapy. Some more common terms for such electrical stimulation therapies include anti-tachycardia pacing (ATP) therapy, cardiac resynchronization therapy (CRT), and cardioversion/defibrillation.

In some examples, LCP 100 may not include pulse generator 104. For example, LCP 100 may be a diagnostic only device. In such examples, LCP 100 may not deliver electrical stimulation therapy to a patient. In such examples, LCP 100 may collect data about cardiac electrical activity and/or physiological parameters of the patient and communicate data or determinations to one or more other medical devices. Accordingly, in such examples, LCP 100 may not need pulse generator 104.

In some examples, LCP 100 may include electrical sensing module 106, and in some cases, mechanical sensing module 108. Electrical sensing module 106 may be configured to sense the cardiac electrical activity of the heart. For example, electrical sensing module 106 may be connected to electrodes 114/114', and electrical sensing module 106 may be configured to receive cardiac electrical signals conducted through electrodes 114/114'. For instance, the cardiac electrical signals may represent local information from the chamber in which LCP 100 is implanted. For instance, if LCP 100 is implanted within a ventricle of the heart, cardiac electrical signals sensed by LCP 100 through electrodes 114/114' may represent ventricular cardiac electrical signals. Mechanical sensing module 108 may include, or be electrically connected to, one or more sensors, such as an accelerometer, a blood pressure sensor, a heart sound sensor, a blood-oxygen sensor, and/or other sensors which are configured to measure one or more physiological parameters of the patient. Both electrical sensing module 106 and mechanical sensing module 108 may further be connected to processing module 110 and provide signals representative of the sensed electrical activity or physiological parameters to processing module 110. Although described with respect to FIG. 1 as separate sensing modules, in some cases, electrical sensing module 106 and mechanical sensing module 108 may be combined into a single sensing module.

Electrodes 114/114' can be secured relative to housing 120 but exposed to the tissue and/or blood surrounding LCP 100. In some cases, electrodes 114 may be generally disposed on either end of LCP 100 and may be in electrical communication with one or more of modules 102, 104, 106, 108, and 110. Electrodes 114/114' may be supported by the housing 120, although in some examples, electrodes 114/114' may be connected to housing 120 only through short connecting wires such that electrodes 114/114' are not directly secured relative to housing 120. In examples where LCP 100 includes one or more electrodes 114', electrodes 114' may be generally disposed on the sides of LCP 100 and may increase the number of electrodes by which LCP 100 may sense cardiac electrical activity, deliver electrical stimulation and/or communicate with an external medical device. Electrodes 114/114' can be made up of one or more biocompatible conductive materials such as various metals or alloys that are known to be safe for implantation within a human body. In some instances, electrodes 114/114' connected to LCP 100 may have an insulative portion that electrically isolates electrodes 114/114' from adjacent electrodes, housing 120, and/or other materials.

Processing module 110 can be configured to control the operation of LCP 100. For example, processing module 110 may be configured to receive electrical signals from electrical sensing module 106 and/or mechanical sensing module 108. Based on the received signals, processing module 110 may determine, for example, occurrences and, in some cases types, of arrhythmias. Based on any determined arrhythmias, processing module 110 may control pulse generator module 104 to generate electrical stimulation in accordance with one or more therapies to treat the determined arrhythmia(s). Processing module 110 may further receive information from communication module 102. In some examples, processing module 110 may use such received information to help determine whether an arrhythmia is occurring, determine a type of arrhythmia, and/or to take particular action in response to the information. Processing module 110 may additionally control communication module 102 to send information to other devices.

In some examples, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other examples, processing module 110 may include a programmable microprocessor. Such a programmable microprocessor may allow a user to adjust the control logic of LCP 100 even after implantation, thereby allowing for greater flexibility of LCP 100 than when using a pre-programmed ASIC. In some examples, processing module 110 may further include a memory circuit, and processing module 110 may store information on and read information from the memory circuit. In other examples, LCP 100 may include a separate memory circuit (not shown) that is in communication with processing module 110, such that processing module 110 may read and write information to and from the separate memory circuit.

Battery 112 may provide a power to the LCP 100 for its operations. In some examples, battery 112 may be a non-rechargeable lithium-based battery. In other examples, a non-rechargeable battery may be made from other suitable materials. Because LCP 100 is an implantable device, access to LCP 100 may be limited after implantation. Accordingly, it is desirable to have sufficient battery capacity to deliver therapy over a period of treatment such as days, weeks, months, years or decades. In other examples, battery 112 may a rechargeable lithium-based battery, which may help increase the useable lifespan of LCP 100. In still other examples, battery 112 may be some other type of power source.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. Anchor 116 may include any one of a number of fixation or anchoring mechanisms. For example, anchor 116 may include one or more pins, staples, threads, screws, helix, tines, and/or the like. In some examples, although not shown, anchor 116 may include threads on its external surface that may run along at least a partial length of anchor 116. The threads may provide friction between the cardiac tissue and the anchor to help fix the anchor 116 within the cardiac tissue. In other examples, anchor 116 may include other structures such as barbs, spikes, or the like to facilitate engagement with the surrounding cardiac tissue.

Figure 2:
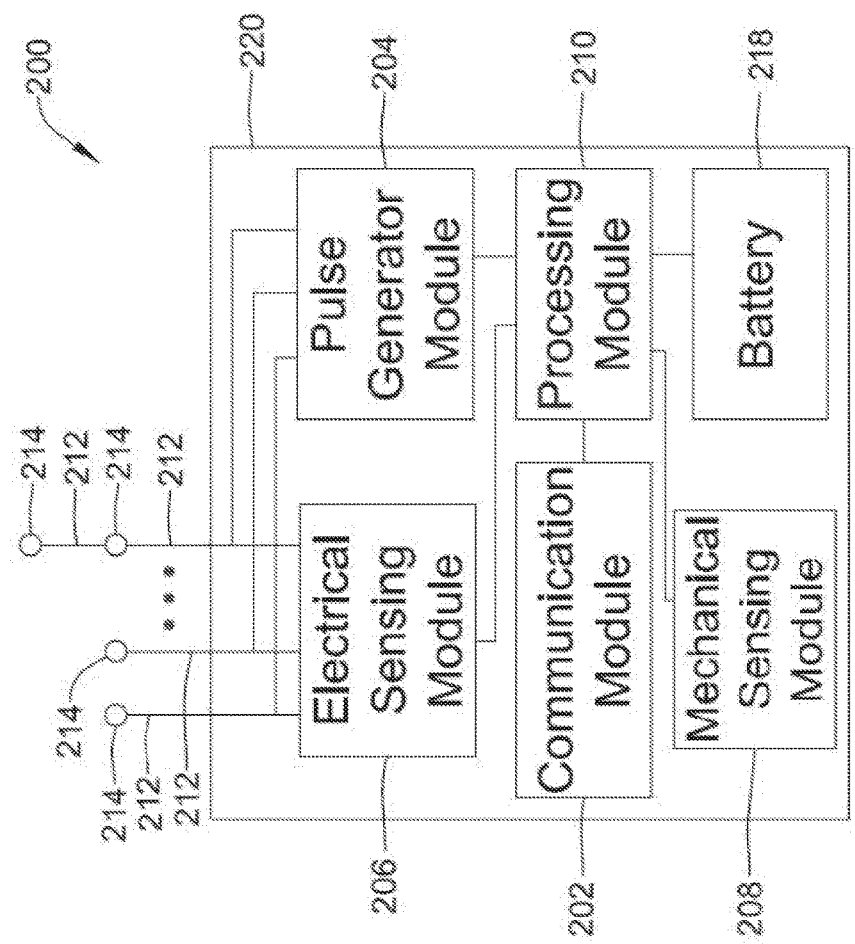
FIG. 2 is a schematic block diagram of another illustrative medical device that may be used in conjunction with the LCP of FIG. 1.

FIG. 2 depicts an example of another device, medical device (MD) 200, which may be used separately or in conjunction with LCP 100 of FIG. 1 in order to detect and treat cardiac arrhythmias and other heart conditions. In the example shown, MD 200 may include a communication module 202, a pulse generator module 204, an electrical sensing module 206, a mechanical sensing module 208, a processing module 210, and a battery 218. Each of these modules may be similar to modules 102, 104, 106, 108, and 110 of LCP 100. Additionally, battery 218 may be similar to battery 112 of LCP 100. However, in some examples, MD 200 may have a larger volume within housing 220. In such examples, MD 200 may include a larger battery and/or a larger processing module 210 capable of handling more complex operations than processing module 110 of LCP 100.

While MD 200 may be another leadless device such as shown in FIG. 1, in some instances MD 200 may include leads such as leads 212. Leads 212 may include electrical wires that conduct electrical signals between electrodes 214 and one or more modules located within housing 220. In some cases, leads 212 may be connected to and extend away from housing 220 of MD 200. In some examples, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In some cases, electrodes 214 may conduct intrinsically generated electrical signals to leads 212, e.g. signals representative of intrinsic cardiac electrical activity. Leads 212 may, in turn, conduct the received electrical signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical signals to the cardiac tissue of the patient.

Mechanical sensing module 208, as with mechanical sensing module 108, may contain or be electrically connected to one or more sensors, such as accelerometers, blood pressure sensors, heart sound sensors, blood-oxygen sensors, and/or other sensors which are configured to measure one or more physiological parameters of the heart and/or patient. In at least some examples, at least some of these examples, one or more of the sensors may be located on leads 212. In such examples, mechanical sensing modules 208 may be in electrical communication with leads 212 and may receive signals generated from such sensors.

While not required, in some examples MD 200 may be an implantable medical device. In such examples, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body.

In some cases, MD 200 may be an implantable cardiac pacemaker (ICP). In this example, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some examples, MD 200 may additionally be configured provide defibrillation therapy.

In some instances, MD 200 may be an implantable cardioverter-defibrillator (ICD). In such examples, MD 200 may include one or more leads implanted within a patient's heart. MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, MD 200 may be a subcutaneous implantable cardioverter-defibrillator (S-ICD). In examples where MD 200 is an S-ICD, one of leads 212 may be a subcutaneously implanted lead. In at least some examples where MD 200 is an S-ICD, MD 200 may include only a single lead which is implanted subcutaneously, but this is not required.

In some examples, MD 200 may not be an implantable medical device. Rather, MD 200 may be a device external to the patient's body, and electrodes 214 may be skin-electrodes that are placed on a patient's body. In such examples, MD 200 may be able to sense surface electrical signals (e.g. cardiac electrical signals that are generated by the heart or electrical signals generated by a device implanted within a patient's body and conducted through the body to the skin). In such examples, MD 200 may be configured to deliver various types of electrical stimulation therapy, including for example defibrillation therapy.

Figure 3:
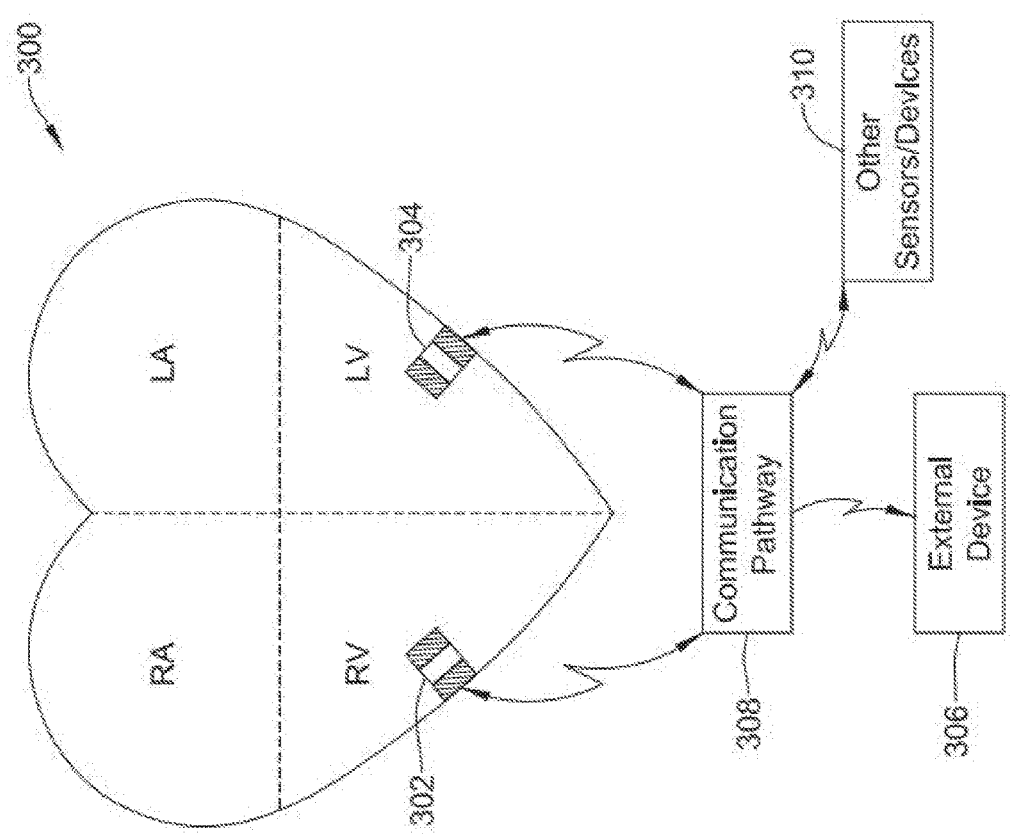
FIG. 3 is a schematic diagram of an exemplary medical system that includes multiple LCPs and/or other devices in communication with one another.

FIG. 3 illustrates an example of a medical device system and a communication pathway via which multiple medical devices may communicate. In the example shown, medical device system 300 may include LCPs 302 and 304, external medical device 306, and other sensors/devices 310. External device 306 may be any of the devices described previously with respect to LCP 100 and MD 200. Other sensors/devices 310 may also be any of the devices described previously with respect to LCP 100 and MD 200. In other examples, other sensors/devices 310 may include a sensor, such as an accelerometer or blood pressure sensor, or the like. In still other examples, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one example, one or more of devices 302/304 may receive such signals and, based on the received signals, determine an occurrence of an arrhythmia. In some cases, device or devices 302/304 may communicate such determinations to one or more other devices 306 and 310 of system 300. Additionally, one or more of devices 302/304, 306, and 310 of system 300 may take action based on the communicated determination of an arrhythmia, such as by delivering a suitable electrical stimulation. It is contemplated that communication pathway 308 may communicate using RF signals, inductive coupling, optical signals, acoustic signals, or any other signals suitable for communication. Additionally, in at least some examples, device communication pathway 308 may include multiple energy types. For instance, other sensors/device 310 may communicate with external device 306 using a first energy type but communicate with LCPs 302/304 using a second energy type. Further, in some examples, communication between devices may be limited. For instance, as described above, in some examples, LCPs 302/304 may communicate with external device 306 only through other sensors/devices 310, where LCPs 302/304 send signals to other sensors/devices 310, and other sensors/devices 310 relay the received signals to external device 306.

In some cases, communication pathway 308 represents a conducted communication pathway. Accordingly, devices of system 300 may have components that allow for such conducted communication. For instance, the devices of system 300 may be configured to transmit conducted communication signals (e.g. pulses) into the patient's body via one or more electrodes of a transmitting device, and may receive the conducted communication signals (e.g. pulses) via one or more electrodes of a receiving device. The patient's body may conduct the conducted communication signals (e.g. pulses) from the one or more electrodes of the transmitting device to the one or more electrodes of the receiving device in the system 300. In such examples, the delivered conducted communication signals (e.g. pulses) may differ from pacing or other therapy signals. For example, the devices of system 300 may deliver electrical communication pulses at an amplitude/pulse width that is sub-threshold to the heart. That is, the communication pulses may have combinations of amplitudes and pulses widths that, when delivered to tissue of the patient, do not cause capture of the heart. Although, in some cases, the amplitude/pulse width of the delivered electrical communication pulses may be above the capture threshold of the heart, but may be delivered during a refractory period of the heart and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired.

Figure 4:
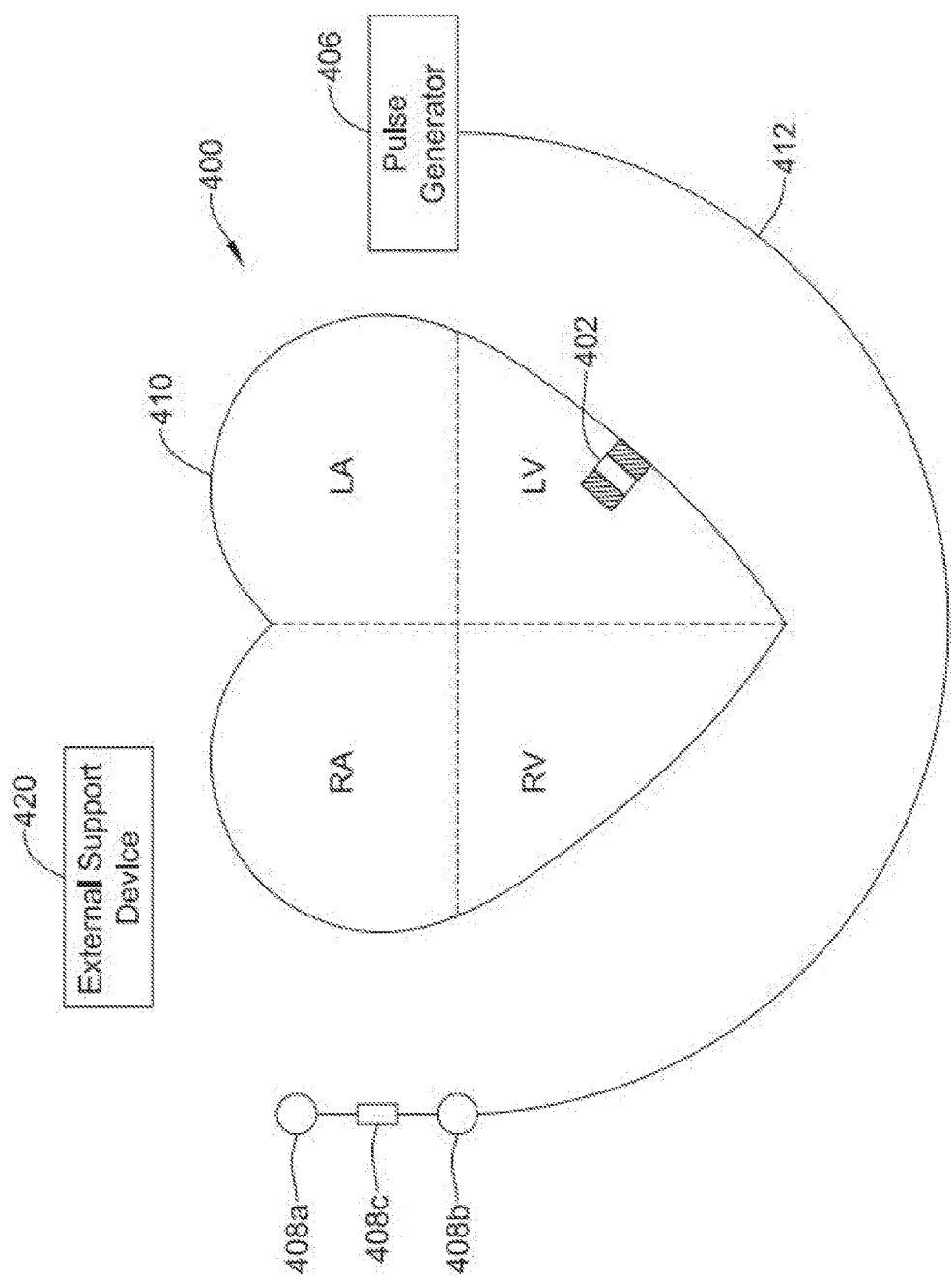
FIG. 4 is a schematic diagram of a system including an LCP and another medical device, in accordance with yet another example of the present disclosure.
Figure 5:
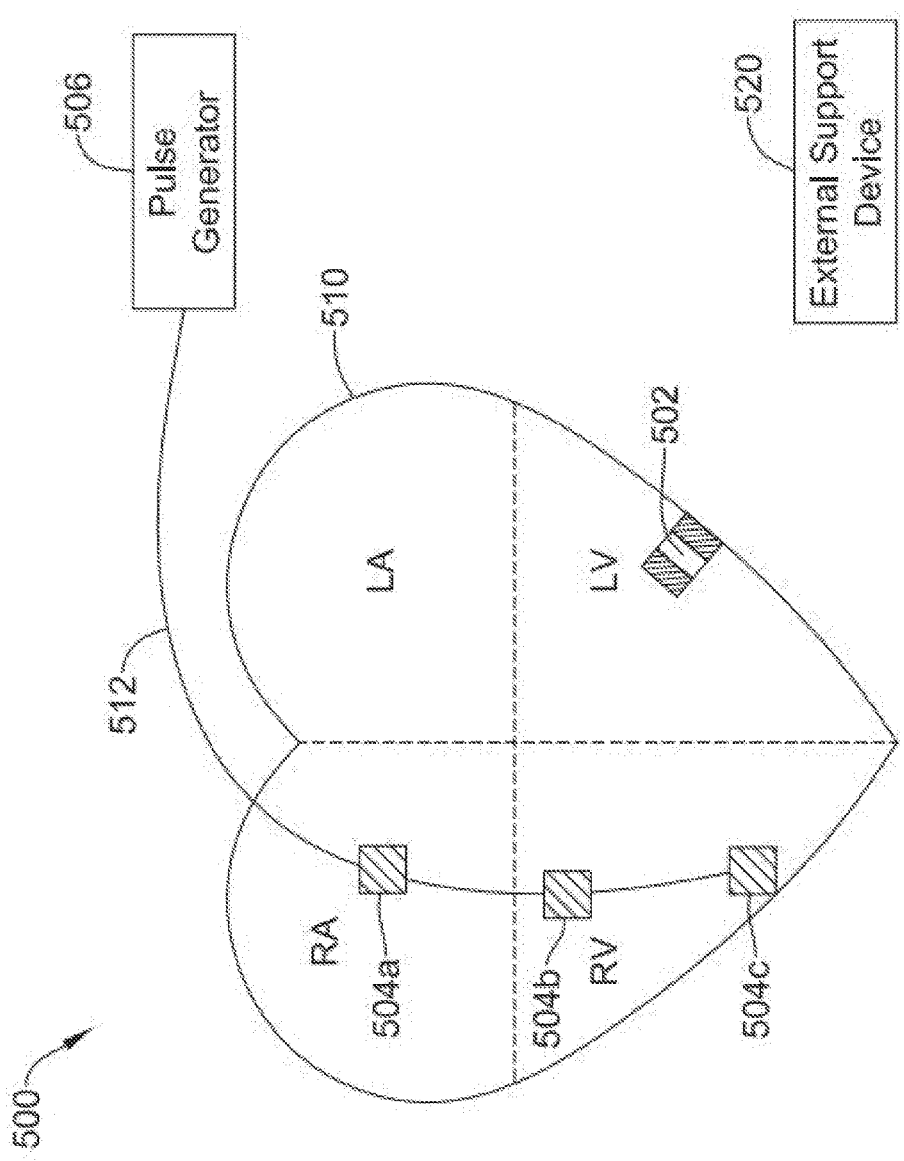
FIG. 5 is a schematic diagram of a system including an LCP and another medical device, in accordance with another example of the present disclosure.

FIGS. 4 and 5 show illustrative medical device systems that may be configured to operate according to techniques disclosed herein. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously adjacent the heart. In some cases, the LCP 402 may communicate with the subcutaneous implantable cardioverter-defibrillator (S-ICD).

In FIG. 5, an LCP 502 is shown fixed to the interior of the left ventricle of the heart 510, and a pulse generator 506 is shown coupled to a lead 512 having one or more electrodes 504a-504c. In some cases, the pulse generator 506 may be part of an implantable cardiac pacemaker (ICP) and/or an implantable cardioverter-defibrillator (ICD), and the one or more electrodes 504a-504c may be positioned in the heart 510. In some cases, the LCP 502 may communicate with the implantable cardiac pacemaker (ICP) and/or an implantable cardioverter-defibrillator (ICD).

The medical device systems 400 and 500 may also include an external support device, such as external support devices 420 and 520. External support devices 420 and 520 can be used to perform functions such as device identification, device programming and/or transfer of real-time and/or stored data between devices using one or more of the communication techniques described herein. As one example, communication between external support device 420 and the pulse generator 406 is performed via a wireless mode, and communication between the pulse generator 406 and LCP 402 is performed via a conducted mode. In some examples, communication between the LCP 402 and external support device 420 is accomplished by sending communication information through the pulse generator 406. However, in other examples, communication between the LCP 402 and external support device 420 may be direct.

Additionally, FIGS. 4 and 5 are only two examples of medical device systems that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs without other devices such as pulse generator 406 or 506, with at least one LCP capable of delivering defibrillation therapy. In yet other examples, the configuration or placement of the medical devices, leads, and/or electrodes may be different from those depicted in FIGS. 4 and 5. Accordingly, it should be recognized that numerous other medical device systems, different from those depicted in FIGS. 4 and 5, may be operated in accordance with techniques disclosed herein. As such, the examples shown in FIGS. 4 and 5 should not be viewed as limiting in any way.

According to some example techniques of the present disclosure, a first medical device may communicate with a second medical device during different periods of time following cardiac events when operating in different communication modes. For example, LCP 402 may be implanted within a patient and communicate information such as sensed physiological signals, determined occurrences of arrhythmias, device diagnostic information and the like to pulse generator 406. In some examples, LCP 402 may be in a first communication mode and configured to communicate during a first time period and may be in a second communication mode and configured to communication during a second time period. In some examples, LCP 402 may switch communication modes based on sensed physiological parameters of the patient. In examples where LCP 402 communicates using energy which may cause stimulation of cardiac tissue, LCP 402 may begin operation in a first communication mode. After determining that communication pulses delivered to tissue of the patient while in the first communication mode do capture the heart of the patient, LCP 402 may switch to a second communication mode. After determining that communication pulses delivered to tissue of the patient do not capture the heart of the patient while in the second communication mode, LCP 402 may switch to the first communication mode. The below described techniques illustrate a number of example communication modes according to which a medical device may operate. The techniques may also illustrate a number of protocols that a device may employ to determine whether communication pulses are capturing the heart of the patient. The described techniques may be described using LCP 402 and/or pulse generator 406 where LCP 402 and pulse generator 406 communicate using conducted communication pulses. However, it should be understood that the described techniques may be applicable to any medical device or medical device system using communication pulses of any type of energy which may cause capture of the heart of the patient. As such, the description herein should not be interpreted as limiting the techniques to only medical devices such as LCP 402 and/or pulse generator 406 and to only the use of conducted communication pulses.

In some examples, LCP 402 may be configured to communicate using conducted communication pulses. More specifically, the conducted communication pulses may be sub-threshold conducted communication pulses which, when delivered to tissue of a patient, do not cause capture of the heart. In such examples, LCP 402 may communicate without interfering with any electrical stimulation therapy currently being implemented by LCP 402, pulse generator 406, and/or another medical device. Accordingly, LCP 402 may be initially configured, such as at the time of implantation, to communicate using conducted communication pulses having a combination of an amplitude and a pulse width which do not cause capture of the heart. For instance, LCP 402 may be preprogrammed to deliver conducted communication pulses with an amplitude and pulse width that have been predetermined to not cause capture in a majority of a patient population. In other examples, LCP 402 may be programmed to deliver conducted communication pulses having a combination of an amplitude and a pulse width that has been predetermined not to cause capture of the heart of the patient in which LCP 402 is implanted or about to be implanted. In still other examples, LCP 402 may be configured to determine one or more combinations of amplitudes and pulse widths for conducted communication pulses which do not cause capture of the heart. In some situations, LCP 402 may determine a combination of an amplitude and/or pulse width for conducted communication pulses using a safety margin. In such examples, LCP 402 may be programmed with or may determine combinations of amplitudes and pulse widths which lie along a threshold where increasing the amplitude and/or pulse width of conducted communication pulses above the threshold may cause capture of the heart and decreasing the amplitude and/or pulse width of conducted communication pulses below the threshold may not cause capture of the hear. LCP 402 may then determine to deliver conducted communication pulses with amplitudes and/or pulse widths that are less than the determined threshold by a safety margin amount.

In the manner above, LCP 402 may be configured to deliver conducted communication pulses with a combination of an amplitude and a pulse width that may not cause capture of the heart of the patient. Each device that may be part of a system with LCP 402 may be also be configured in similar manners. In some examples, other medical devices may be configured to deliver conducted communication pulses with different amplitudes and/or pulse widths than LCP 402 because the specific positions of the devices within the patient as well as potentially differently shaped and/or spaced electrodes may affect the amplitudes and/or pulse widths at which conducted communication pulses delivered by the other medical devices capture the heart of the patient. The below described techniques detail various techniques for switching communication modes after determining that delivered conducted communication pulses have captured the heart of the patient. The techniques also describe different protocols that LCP 402 or other devices may use to determine if conducted communication pulses are capturing the heart of the patient and various communication modes defining when LCP 402 or other devices may deliver conducted communication pulses.

Figure 6:
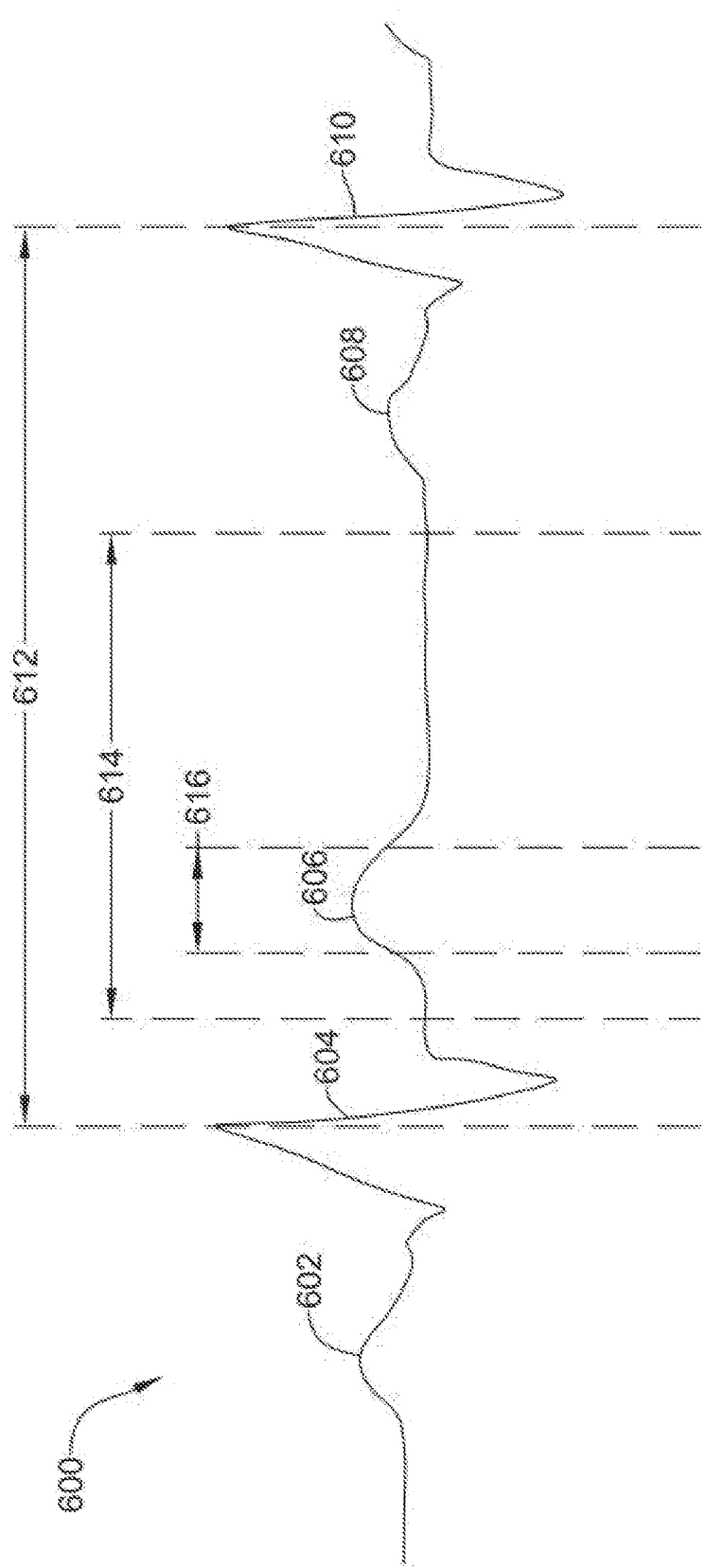
FIG. 6 is a graph of an example cardiac cycle and times during the cardiac cycle when a medical device may deliver conducted communication pulses to tissue of a patient, in accordance with an example of the present disclosure.

FIG. 6 depicts an example timing diagram of a normal cardiac cycle and times during the cardiac cycle when a medical device might deliver conducted communication pulses to tissue of a patient when in a first communication mode. Specifically, FIG. 6 depicts example ECG waveform 600 including a number of different intervals. Two example beats of a heart are depicted with the first beat indicated by P-wave 602, QRS complex 604, and T-wave 606 and the second beat indicated by P-wave 608 and QRS complex 610. A cardiac interval, representing the time between heartbeats is represented by cardiac interval 612, which spans the distance between QRS complex 604 and QRS complex 610. Communication interval 614 may represent an period of time during which a medical device, such as LCP 402, is configured to communicate, e.g. deliver conducted communication pulses to the tissue of the patient, when operating in a first communication mode. Portions of this disclosure may refer to communication interval 614 as a first communication window. Communication interval 614 is generally depicted as spanning a portion of cardiac interval 612, sometimes excluding QRS complexes and P-waves. In such examples, communication interval 614 may begin a predetermined amount of time after a detected R-wave. Some example predetermined times include fifty, one-hundred, two-hundred, five-hundred milliseconds, one thousand milliseconds, or any other suitable amount of time after a detected R-wave. In at least one example, communication interval 614 may begin after a refractory period of the heart. In other examples, however, communication interval 614 may span other portions of cardiac interval 612. For example, communication interval 614 may span all of cardiac interval 612.

FIG. 6 also depicts a vulnerable period 616. Vulnerable period 616 is a portion of cardiac interval 612 coinciding with a period of the cardiac cycle when a delivered conducted pulse is more likely to cause a tachyarrhythmic episode. Vulnerable period 616 generally coincides with a portion of the T-wave including the portion of the T-wave just before the apex and running to just after the apex.

Upon initial set-up, LCP 402 and/or the other medical devices may be configured such that conducted communication pulses delivered during communication interval 614 do not result in capture of the heart of the patient. For example, the pulse amplitude and/or pulse width of the communication pulses may be set so as to not result in capture of the heart of the patient. However, due to physiological or other changes, in some instances the conducted communication pulses delivered by one or more of the medical devices may begin to cause capture of the heart. Such circumstances may become dangerous for the patient, as the delivered conducted communication pulses may begin to interfere with implemented electrical stimulation therapy or an intrinsic rhythm of the heart. Accordingly, and in this example, LCP 402 and/or the other medical devices may be configured to determine whether delivered conducted communication pulses in a first communication mode capture the heart of the patient and, if so under some circumstances, switch to a second communication mode which may be safer for the patient. FIGS. 7-11 depict various techniques for determining that delivered conducted communication pulses are capturing the heart.

Figure 7:
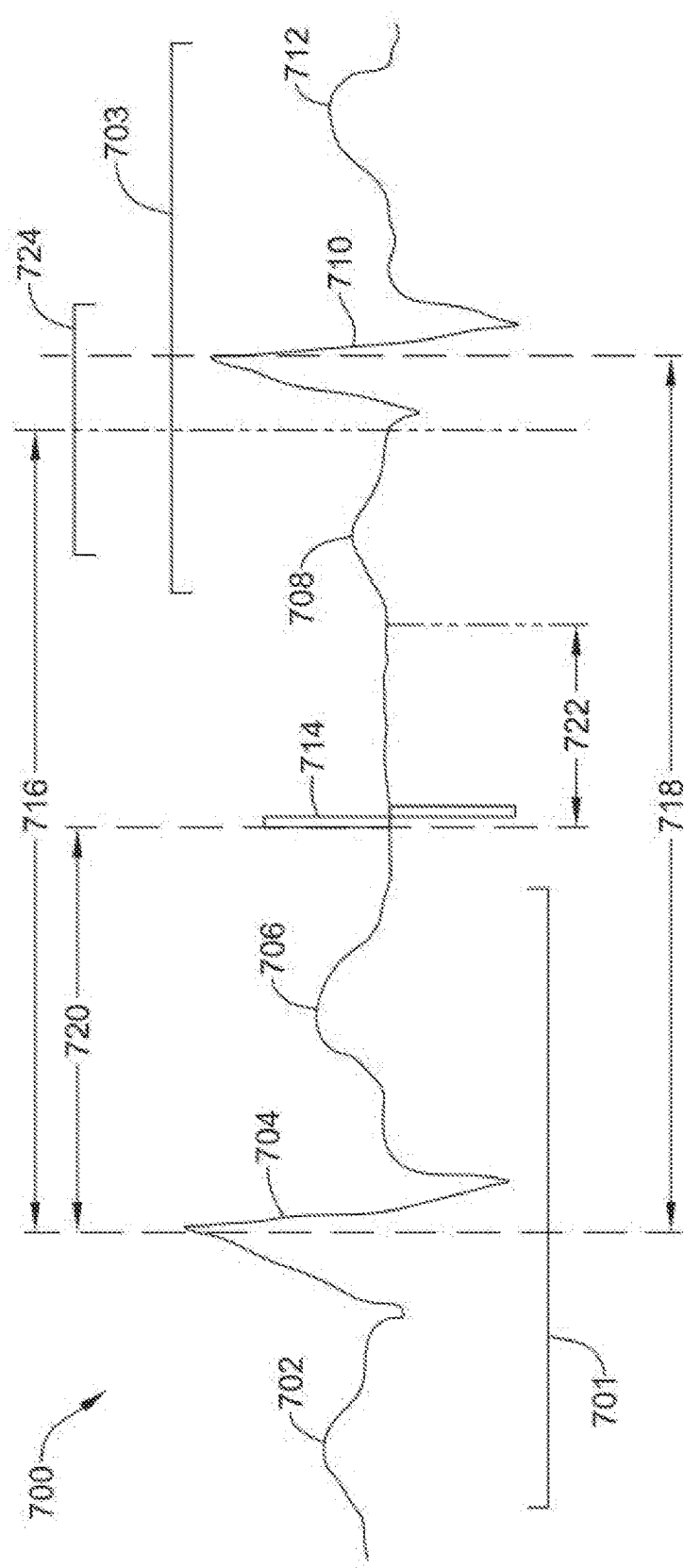
FIG. 7 is a graph of an example cardiac cycle and illustrates an example technique for determining whether delivered conducted communication pulses capture the heart, in accordance with an example of the present disclosure.

FIG. 7 illustrates a first example technique for determining whether delivered conducted communication pulses are capturing the heart. FIG. 7 illustrates an example ECG waveform 700 having exemplary beats 701 and 703. The first beat, beat 701, is represented by P-wave 702, QRS complex 704, and T-wave 706, and the second beat, beat 703, is represented by P-wave 708, QRS complex 710, and T-wave 712. Prior to beats 701 and 703 depicted in FIG. 7, LCP 402 may have determined an intrinsic cardiac interval between beats. For example, LCP 402 may have determined the intrinsic cardiac interval between beats by monitoring an elapsed time between two (or more) prior consecutive intrinsic beats. In some cases, LCP may identify beats by detecting R-waves, detecting timings of maximum negative derivatives of the ECG waveform, detecting heart sounds, detecting cardiac impedance changes, detecting cardiac motion, or by using some other beat detection scheme. In some examples, the intrinsic cardiac interval may include the elapsed time between the two prior consecutive heartbeats. In other examples, the intrinsic cardiac interval may include an average of the elapsed time between multiple prior consecutive beats, for example the last ten, eight, five, or three beats.

After determining an intrinsic cardiac interval, LCP 402 may identify a first beat, such as beat 701 and, from beat 701, determine an estimated timing of when the next beat should occur using the determined intrinsic cardiac interval. In FIG. 7, the end of estimation interval 716 represents the estimated timing of the next beat after beat 701, where the length of estimation interval 716 is based on the determined cardiac interval. FIG. 7 depicts LCP 402 identifying beats based on the R-wave peaks of the sensed QRS complexes 704 and 710 and using the R-wave peaks for measuring various intervals, such as estimation interval 716 and wait interval 720. However, as discussed above, LCP 402 may identify beats according to any beat detection schemes and may use any particular feature of the identified beats for measuring intervals.

Once LCP 402 has determined the estimated timing of the next beat, LCP 402 may wait a predetermined amount of time from beat 701, identified by wait interval 720, and then deliver conducted communication pulse 714 to tissue of the patient. Some example times for wait interval 720 may include two-hundred fifty milliseconds, three hundred milliseconds, three-hundred fifty milliseconds, four hundred milliseconds, and four-hundred fifty milliseconds, or any other suitable length of time. However, in at least some examples, wait interval 720 may be determined at least in part based on estimation interval 716. For example, wait interval 720 may be a certain percentage of estimation interval 716, or wait interval 720 may be determined based on a non-linear function where estimation interval 716 is one parameter of the function. In other examples, wait interval 720 may be based on the vulnerable period of beat 701. For example, LCP 402 may determine when the vulnerable period for beat 701 occurs, such as by identifying the beginning and/or ending of T-wave 706. Although, in other examples, LCP 402 may use a predictive method for determining the vulnerable period for beat 701 by determining timings for vulnerable periods for preceding beats and applying the determined timings to beat 701. LCP 402 may then determine that wait interval 720 is ten, twenty-five, or fifty milliseconds long, or any other suitable length of time, after the end of the vulnerable period of beat 701. Additionally in some examples, LCP 402 may be configured to not deliver any conducted communication pulses if wait interval 720 ends less than one hundred milliseconds (or other determined time period) before the next beat is estimated to occur.

Conducted communication pulse 714 may have an amplitude and pulse width that LCP 402 is currently programmed to deliver during communication sessions. Although depicted in FIG. 7 as a biphasic conducted communication pulse, in other examples conducted communication pulse 714 may be monophasic or may include any particular morphology. After delivering conducted communication pulse 714, LCP 402 may implement a blanking period, represented by blanking period 722, during which LCP 402 does not sense for cardiac electrical activity or other conducted electrical activity. However, in other examples LCP 402 may not include a blanking period.

Once LCP 402 senses a next beat, LCP 402 may identify the actual timing difference between beat 701 and the next beat, which in the example of FIG. 7 is beat 703. The determined difference in timings between beat 701 and beat 703 is represented by interval 718. If beat 703, or more specifically in the example of FIG. 7 the R-wave of QRS complex 710 of beat 703, occurs after the end of estimation interval 716, LCP 402 may determine that conducted communication pulse 714 did not capture the heart. In such examples, estimation interval 716 would be similar in value to interval 718. Conversely, if beat 703 occurs before the end of estimation interval 716, LCP 402 may determine that conducted communication pulse 714 did capture the heart. In some examples, LCP 402 may employ a window around the end of estimation interval 716, represented in FIG. 7 by window 724, for purposes of determining whether conducted communication pulse 714 captured the heart. Window 724 may include ten, twenty-five, forty, or fifty milliseconds, or any other suitable amount of time, before and after the end of the estimation interval 716. In other examples, window 724 may have a width that is a percentage of estimation interval 716. For example, window 724 may have a width of five, ten, fifteen, twenty percent, or any other suitable percent of estimation interval 716. LCP 402 may determine that conducted communication pulse 714 did not cause capture of the heart if LCP 402 determines that beat 703 fell within window 724, as in FIG. 7. In situations where LCP 402 determines that beat 703 did not fall within window 724, such as occurring before window 724, the LCP 402 may determine that conducted communication pulse 714 did cause capture of the heart.

Figure 8:
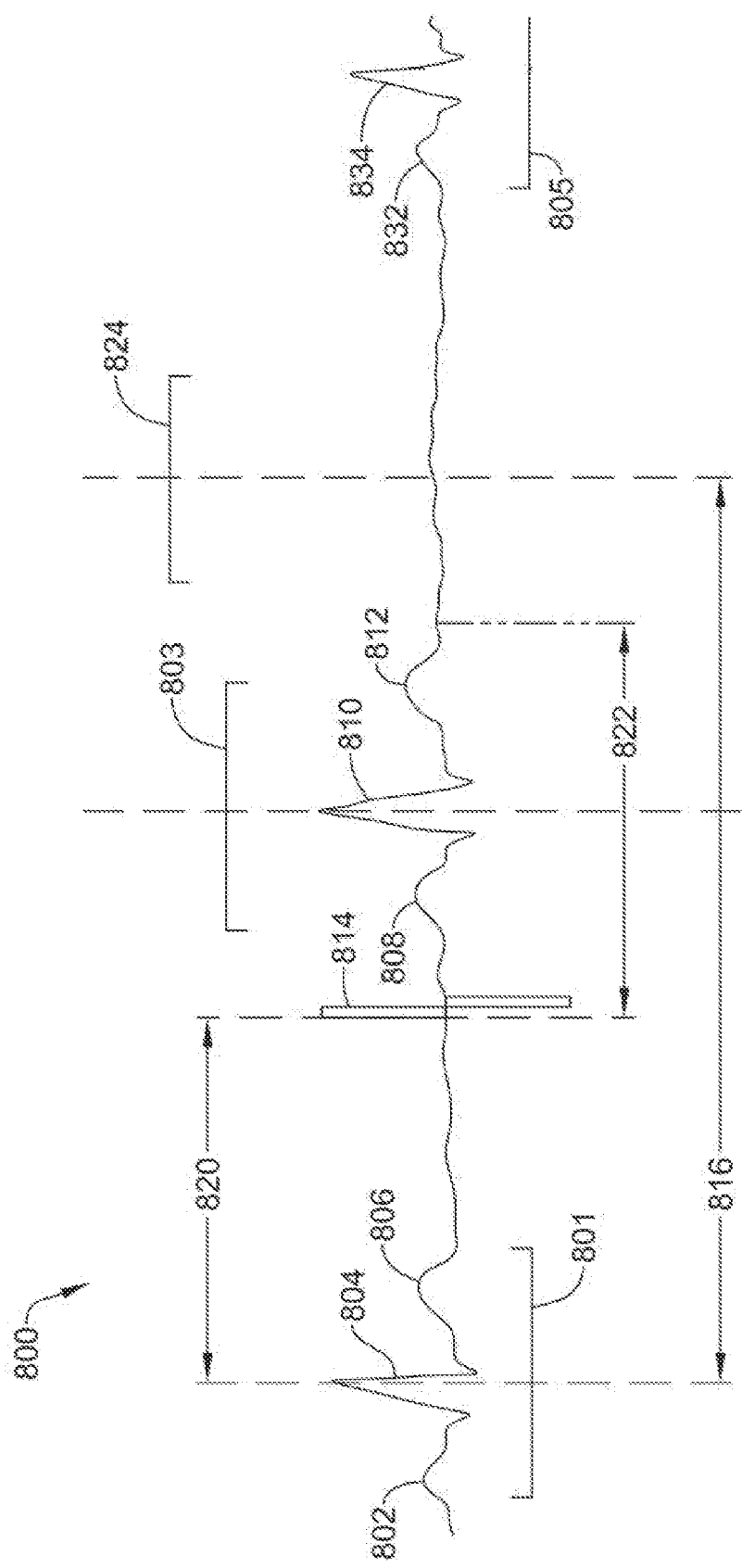
FIG. 8 is a graph of an example cardiac cycle and illustrates an example technique for determining whether delivered conducted communication pulses capture the heart, in accordance with an example of the present disclosure.

FIG. 8 illustrates the example technique described in FIG. 7 where a conducted communication pulse causes capture of the heart. FIG. 8 depicts an ECG waveform 800 that includes exemplary beats 801, 803, and 805. Beat 801 is represented by P-wave 802, QRS complex 804, and T-wave 806. Beat 803 is represented by P-wave 808, QRS complex 810, and T-wave 812. Beat 805 is represented by P-wave 832 and QRS complex 838. FIG. 8 also depicts wait interval 820, estimation interval 816, blanking period 822, window 824, and conducted communication pulse 814. In the example of FIG. 8, conducted communication pulse 814 does capture the heart, as can be seen by beat 803 occurring shortly after conducted communication pulse 814. In the example of FIG. 8, since beat 803 occurs during blanking period 822, LCP 402 does not sense beat 803. Instead, the LCP 402 senses the following beat 805. Since beat 805 falls after the end of estimation interval 816, LPC 402 may determine that conducted communication pulse 814 captured the heart. In other examples, LCP 402 may employ window 824. Since beat 805 does not fall within window 824, LCP 402 may determine that conducted communication pulse 814 caused capture of the heart.

Regardless of the specific protocol in which LCP 402 determines whether a conducted communication pulse 714/814 captured the heart, LCP 402 may take one or more actions when LCP 402 determines that a conducted communication pulse 714/814 captured of the heart. As one example, LCP 402 may switch to a second communication mode. Various exemplary second communication modes are described below with respect to FIGS. 13 and 14 which LCP 402 may implement when in the second communication mode. It should be noted that LCP 402, in performing any of the above described techniques for determining whether conducted communication pulses captured the heart, LCP 402 may perform any of the delivering of conducted communication pulses steps only during times when LCP 402 is configured to deliver conducted communication pulses when in the first communication mode. Additionally, it should also be understood that before, after, and/or during any of the above described techniques, LCP 402 may be performing normal communication functions, such as delivering conducted communication pulses in order to communicate information to other devices.

LCP 402 may be configured, in some examples, to perform the above described example techniques periodically to determine whether conducted communication pulses are capturing the heart. For example, LCP 402 may perform the above described techniques once a day, once a week, once a month, or any other suitable period of time. In some examples, before LCP 402 determines whether conducted communication pulses are capturing the heart, LCP 402 may perform a number of tests as described above. In such examples, LCP 402 may only determine that conducted communication pulses are capturing the heart if a LCP 402 determines that a majority of a plurality of tests resulted in capture the heart, or if LCP 402 determines that a threshold number of a plurality of tests captured the heart. In some examples, LCP 402 may additionally, or alternatively, be configured to perform one or more of the above described techniques after receiving a command to perform a capture test from another device. For example, another device may periodically request that LCP 402 perform one or more capture tests, or may make a request based on values of one or more parameters. In some examples, the other device may be a device programmer used in conjunction with programming sessions, such as during hospital or clinic visits by the patient. In other example, the other device may be another implantable medical device, such as a LCP or an SICD.

Figure 9:
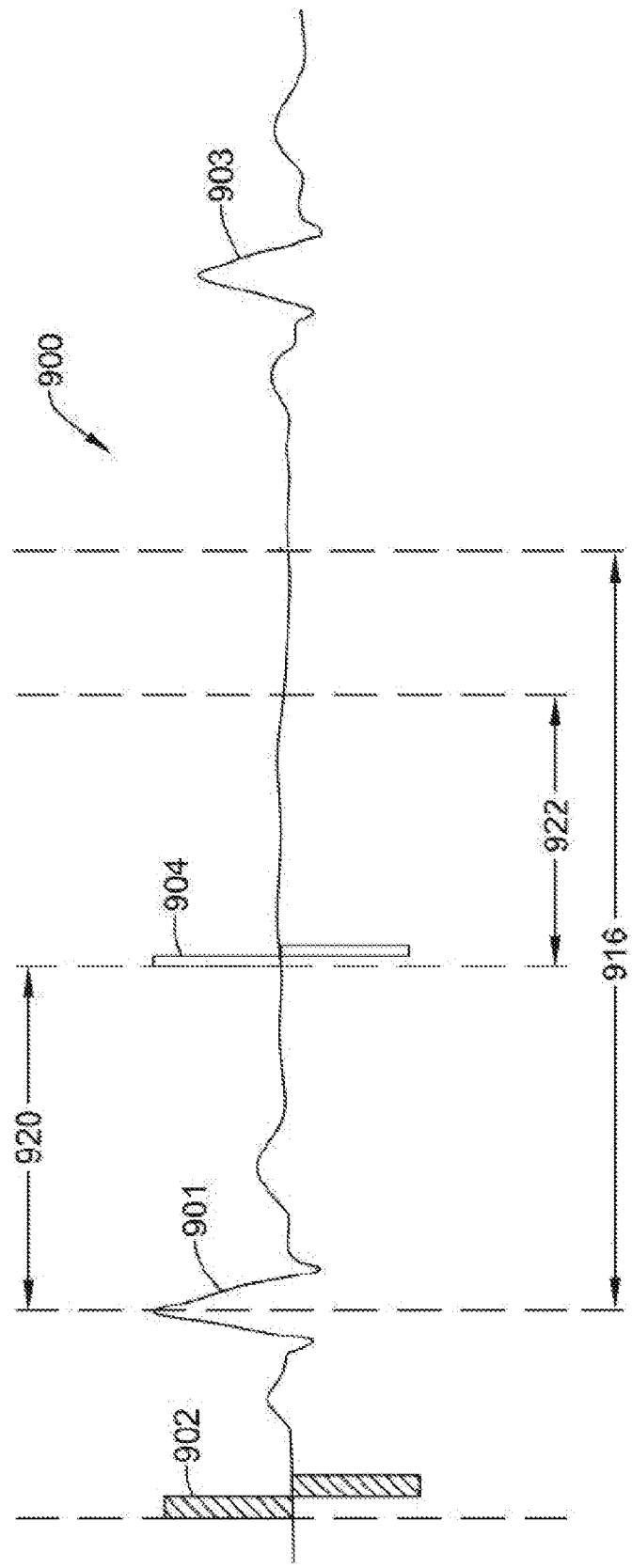
FIG. 9 is a graph of an example cardiac cycle and illustrates an example technique for determining whether delivered conducted communication pulses capture the heart, in accordance with an example of the present disclosure.

FIG. 9 illustrates another example technique for determining whether delivered conducted communication pulses are capturing the heart. FIG. 9 shows an example ECG waveform 900 that includes exemplary beats 901 and 903. LCP 402 may begin by identifying a first beat, such as beat 901. In some examples, the identified first beat is an intrinsic beat. However, in other examples, such as shown in FIG. 9, the identified first beat may be a paced beat. For instance, LCP 402, or another medical device, may deliver a pacing pulse 902 to the heart causing the heart to contract, which results in beat 901.

After identifying beat 901, LCP 402 may wait a predetermined amount of time from beat 901, identified by wait interval 920, and then deliver conducted communication pulse 904 to tissue of the patient. Conducted communication pulse 904 may have an amplitude and pulse width that LCP 402 is currently programmed to deliver during communication sessions. Although depicted in FIG. 9 as a biphasic conducted communication pulse, in other examples conducted communication pulse 904 may have any suitable morphology. Some example times for wait interval 920 include two-hundred fifty milliseconds, three hundred milliseconds, three-hundred fifty milliseconds, four hundred milliseconds, and four-hundred fifty milliseconds, or any other suitable length of time. In other examples, wait interval 920 may be determined at least in part based on a heartbeat rate. For example, LCP 402 may determine a heartbeat rate—e.g. an intrinsic cardiac interval as described with respect to FIG. 7—or another medical device may determine a heartbeat rate and communicate the heartbeat rate to LCP 402. In such examples, wait interval 920 may be a function of the heartbeat rate. For instance, wait interval 920 may be a certain percentage of the determined heartbeat rate, or be determined based on a function including the determined heartbeat rate.

In still other examples, LCP 402 may determine when the vulnerable period for beat 901 occurs. To determine the vulnerable period for beat 901, LCP 402 may identify the beginning and ending of the T-wave of beat 901. Although, in other examples, LCP 402 may use a predictive method for determining the vulnerable period for beat 901 by determining timings for vulnerable periods for preceding beats and applying the determined timings to beat 901. LCP 402 may then determine the wait interval 920 to be is ten, twenty-five, or fifty milliseconds long, or any other suitable length of time, after the end of the vulnerable period of beat 901. In other examples, instead of measuring an interval from beat 901, LCP 402 may wait a predetermined amount of time from pacing pulse 902.

After delivering conducted communication pulse 904, LCP 402 may determine whether a beat occurs within a predetermined period of time after delivering conducted communication pulse 904. In FIG. 9, this period of time is represented by sense interval 922. In some examples, sense interval 922 may be twenty-five, forty, or fifty milliseconds longs, or any other suitable length of time. In the example of FIG. 9, LCP 402 may determine that no beat occurred within sense interval 922 and, accordingly, may determine that conducted communication pulse 904 did not capture the heart.

In some examples, LCP 402 may additionally be configured to determine an estimated timing of the next beat after beat 901, as in the example techniques of FIGS. 7 and 8. For instance, LCP 402 may be configured to determine an estimation interval 916. In at least one example, and as with the example techniques illustrated in FIGS. 7 and 8, prior to beat 901 LCP 402 may have determined an intrinsic cardiac interval. In examples where LCP 402, or another device, is implementing an electrical stimulation therapy program that includes delivering pacing pulses to the heart, LCP 402 may determine the pacing interval, with the pacing interval being the time between successive pacing pulses. LCP 402 may use either the determined intrinsic cardiac interval or the determined pacing interval as estimation interval 916. LCP 402 may then determine that the end of estimation interval 916, as measured from beat 901, is the estimated timing of the next beat after beat 901. In any of these examples where LCP 402 determines an estimated timing of the next beat after beat 901, LCP 402 may be configured to not deliver any conducted communication pulses 904 if wait interval 920 ends less than one hundred milliseconds (or other predetermined time period) before the next beat is estimated to occur.

Figure 10:
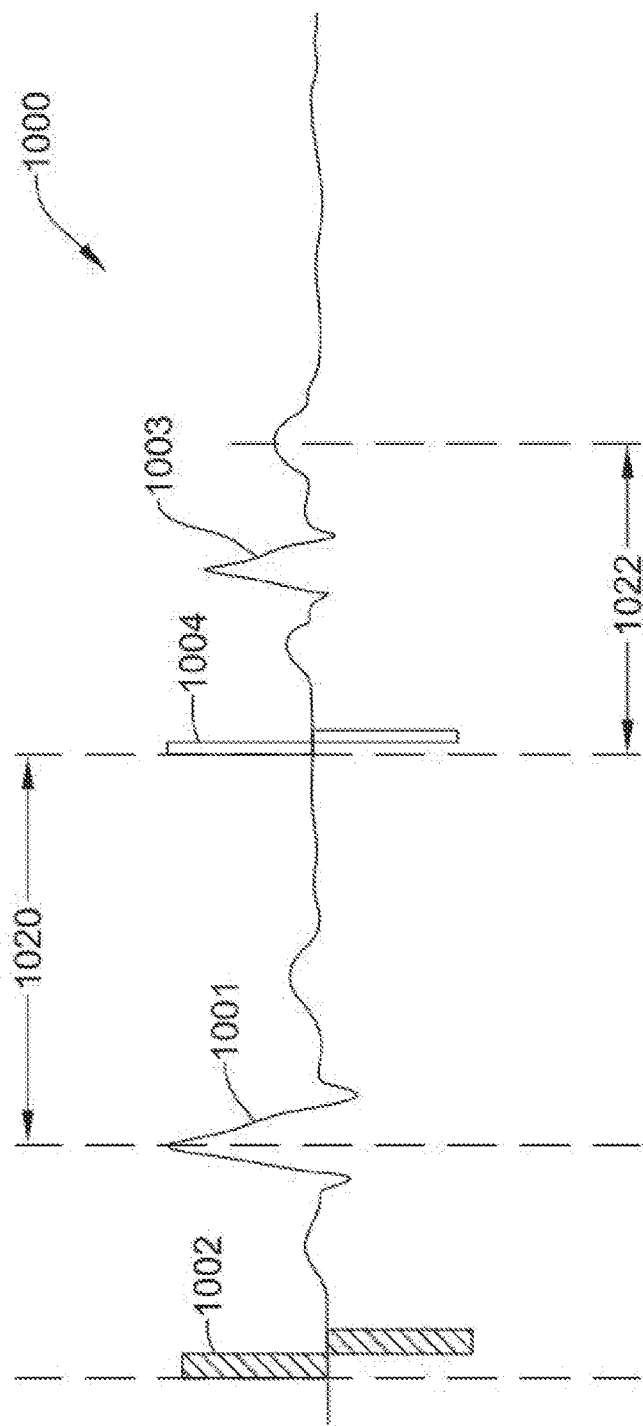
FIG. 10 is a graph of an example cardiac cycle and illustrates an example technique for determining whether delivered conducted communication pulses capture the heart, in accordance with an example of the present disclosure.

FIG. 10 depicts the example technique described with respect to FIG. 9, except the conducted communication pulse causes capture of the heart. Specifically, FIG. 10 depicts pacing pulse 1002, which may be delivered by LCP 402 or another medical device. Pacing pulse 1002 causes capture of the heart resulting in beat 1001 on ECG waveform 1000. As described with respect to FIG. 9, LCP 402 may then wait a predetermined amount of time from beat 1001 before delivering conducted communication pulse 1004, represented by wait interval 1020. After delivering communication pulse 1004, LCP 402 may sense for a beat during sense interval 1022. In the example of FIG. 10, LCP 402 senses beat 1003 during sense interval 1022. Accordingly, LCP 402 may determine that communication pulse 1004 caused capture of the heart. As described with respect to FIG. 9, LCP 402 may be configured to not deliver any conducted communication pulses if wait interval 1020 ends less than one hundred milliseconds (or other predetermined time period) before the next beat is estimated to occur, which is illustrated in FIG. 10 by the end of estimation interval 1016.

In the example of FIG. 10, since LCP 402 detected beat 1003 during sense interval 1022, LCP 402 may determine that communication pulse 1004 caused capture of the heart. Accordingly, LCP 402 may take one or more actions based on the determination. For example, LCP 402 may switch to a second communication mode. Various example second communication modes are described below with respect to FIGS. 13 and 14 which LCP 402 implement when in the second communication mode. It should be noted that LCP 402, in performing any of the above described techniques for determining whether conducted communication pulses captured the heart, LCP 402 may perform any of the delivering of conducted communication pulses steps only during times when LCP 402 is configured to deliver conducted communication pulses when in the first communication mode. Additionally, it should also be understood that before, after, and/or during any of the above described techniques, LCP 402 may be performing normal communication functions, such as delivering conducted communication pulses in order to communicate information to other devices.

LCP 402 may be configured, in some examples, to perform the above described example techniques periodically to determine whether conducted communication pulses are capturing the heart. For example, LCP 402 may perform the above described techniques once a minute, once an hour, once a day, once a week, once a month, or any other suitable period of time. In some examples, before LCP 402 determines whether conducted communication pulses are capturing the heart, LCP 402 may perform a plurality of such tests as described above. In such examples, LCP 402 may only determine that conducted communication pulses are capturing the heart if a LCP 402 determines a majority of a plurality of tests result in capture the heart, or if LCP 402 determines that a threshold number of the plurality of tests resulted in capture of the heart. In some examples, LCP 402 may additionally, or alternatively, be configured to perform the above described techniques after receiving a command from another device to perform one or more such capture tests. For example, another device may periodically request LCP 402 to perform one or more capture tests, or may communicate a request based on values of one or more other parameters. In some examples, the other device may be a device programmer used in conjunction with programming sessions, such as during hospital or clinic visits by the patient. In one examples, the other device may be another implantable medical device such a LCP or an SICD.

There may be short-term variability in the energy required to stimulate cardiac tissue via a communication pulse. For example, the required stimulation energy may vary with patient posture or respiratory cycle. To better ensure communication pulses will not cause cardiac stimulation, the energy used during the capture tests described in FIGS. 6-10 may be higher than that used during communication. For example, the energy of the communication pulse or pulses used during any of the capture tests described with respect to FIGS. 6-10 may be twenty-five percent, fifty percent, one hundred percent, or any other suitable percentage larger than the energy of communication pulses used during normal communication. In this way a margin is introduced between the communication pulses used for the capture test or tests and the communication pulses used during normal communication. For instance without a margin, even if capture tests indicated no stimulation of the cardiac tissue, if the communication pulses used during normal communication had the same energy as the communication pulses used during the capture tests, the communication pulses used during normal communication may stimulate the cardiac tissue as the energy required to stimulate cardiac tissue may vary. Accordingly, introducing an energy margin between the communication pulses used for the capture test or tests and the communication pulses used for normal communication helps to ensure that, even with natural variability in the energy level of communication pulses needed to stimulate cardiac tissue, the communication pulses used for normal communication will not stimulate the cardiac tissue without a capture test detecting stimulation of cardiac tissue by communication pulses.

The energy level of the communication pulses may be based on the morphology of the communication pulses. For example, on a voltage versus time graph, the area under the communication may be one measure of the energy of the communication pulses. In such examples, varying the voltage amplitude, the pulse width, or both will affect the total energy of the communication pulses. Accordingly, the communication pulses used during the capture test or tests may have larger amplitudes, pulse widths, or both to achieve a higher energy level than those communication pulses used during normal communication.

Figure 11:
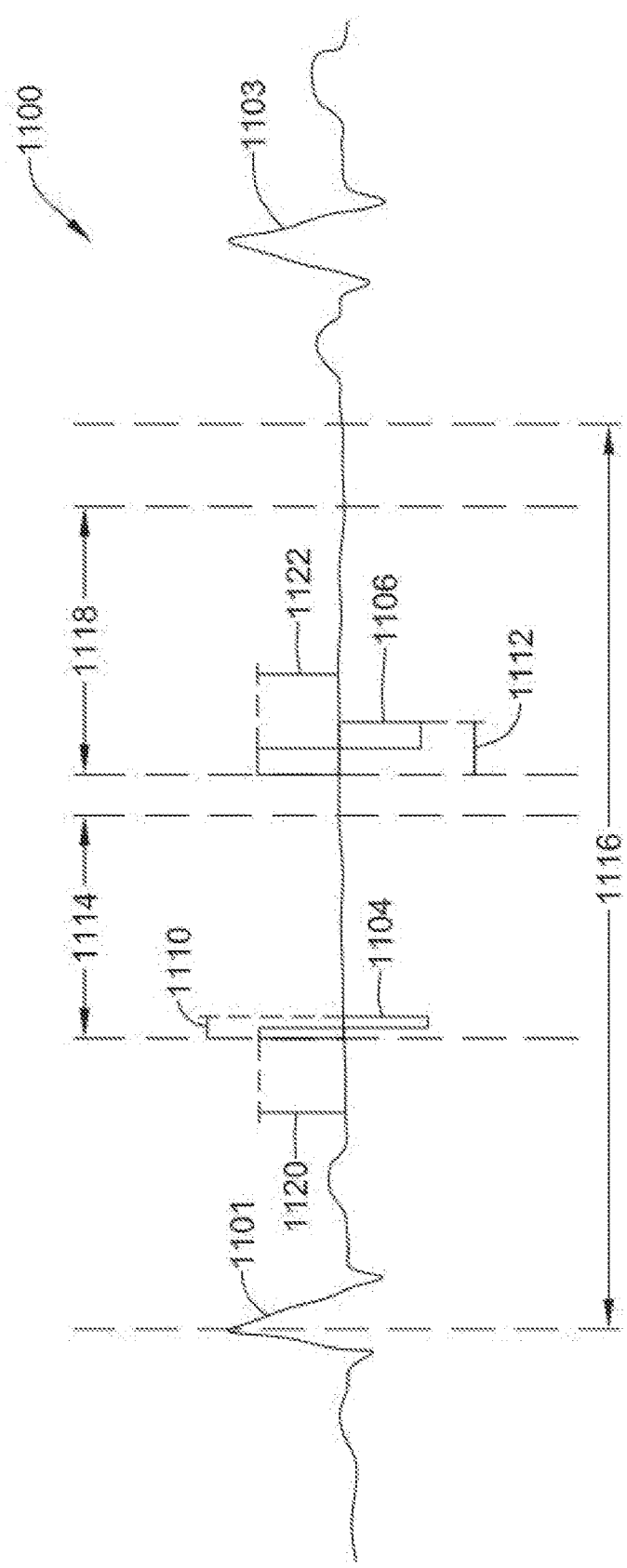
FIG. 11 is a graph of an example cardiac cycle and illustrates an example technique for determining whether delivered conducted communication pulses capture the heart, in accordance with an example of the present disclosure.

FIG. 11 depicts an ECG waveform 1100 that provides an example technique where LCP 402 may deliver multiple conducted communication pulses in order to identify combinations of parameters of conducted communication pulses which cause capture of the heart. For example, it may sometimes be beneficial for LCP 402 to determine combinations of communication pulse parameters that cause capture of the heart rather than solely determining whether a conducted communication pulse did cause capture. In the example of FIG. 11, LCP 402 may be configured to determine whether a conducted communication pulse captures the heart of a patient in accordance with the techniques described above with respect to FIGS. 9 and 10. However, in the example of FIG. 11, LCP 402 may be further configured to change the combinations of parameters of the delivered conducted communication pulses. For example, LCP 402 may modify the amplitude and/or pulse width of the delivered conducted communication pulse or pulses to be different than the amplitude and/or pulse width of the conducted communication pulses used during communication sessions.

As illustrated in FIG. 11, each of conducted communication pulses 1104 and 1106 have an amplitude and a pulse width. Conducted communication pulse 1104 has pulse width 1110 and amplitude 1120. Conducted communication pulse 1106 has pulse width 1112 and amplitude 1122. In the example of FIG. 11, LCP 402 may be configured to implement a sense interval after delivering conducted communication pulse 1104, represented by sense interval 1114. If LCP 402 senses a beat during sense interval 1114, LCP 402 may determine that the combination of pulse width 1110 and amplitude 1120 of conducted communication pulse 1104 caused capture of the heart. However, if LCP 402 does not sense a beat during sense interval 1114, LCP 402 may be configured to deliver another conducted communication pulse, conducted communication pulse 1106, either at the end of sense interval 1114, a predetermined period of time after sense interval 1114, or at any other suitable time. As depicted in FIG. 11, amplitude 1122 of conducted communication pulse 1106 may be the same as amplitude 1120, but pulse width 1112 may be greater than pulse width 1110. LCP 402 may further sense for a beat after delivering conducted communication pulse 1106 during another sense interval, such as sense interval 1118.

LCP 402 may repeat the above described process, increasing pulse widths of delivered conducted communication pulses until sensing a beat during a sense interval, indicating that the delivered conducted communication pulse captured the heart. This may indicate a first capture threshold for the heart—e.g. a specific combination of pulse amplitude and pulse width of communication pulses that, when delivered to the heart, cause capture of the heart. LCP 402 may store the parameters of conducted communication pulses that caused capture of the heart in a memory or communicate the parameters to another device for storage.

In some examples, LCP 402 may be configured to withhold delivering another conducted communication pulse if LCP 402 determines that a next delivered conducted communication pulse would be delivered within one-hundred milliseconds (or another predetermined time period) of when the next beat is expected to occur (whether an intrinsic beat or a paced beat). As illustrated in FIG. 11, LCP 402 may determine that the next beat is expected to occur at the end of estimation interval 1116. A beat 1103, for example, is shown as occurring after the end of the estimation interval 1116. LCP 402 may determine estimation interval 1116 in a similar manner to other estimation intervals disclosed with respect to FIGS. 7-10. Accordingly, if LCP 402 determines that delivering a next conducted communication pulse would fall within one-hundred milliseconds (or other predetermined time period) of the end of estimation interval 1116, LCP 402 may withhold delivering the next conducted communication pulse and wait until after the next detected beat to continue the process. Additionally, although described with respect to increasing pulse widths, in other examples, LCP 402 may be configured to deliver conducted communication pulses starting with relatively large pulse widths and decrease the pulse widths of subsequently delivered conducted communication pulses. In such examples, LCP 402 may sense for absences of beats during sense intervals to detect lack of capture.

Of course, in other examples, LCP 402 may be configured to adjust the parameters of the delivered conducted communication pulses in different ways. For example, instead of adjusting the pulse width, LCP 402 may be configured to adjust the amplitude of the conducted communication pulses. In still other examples, LCP 402 may be configured to adjust both the pulse width and amplitude simultaneously. Additionally, in other examples, LCP 402 may be configured to deliver communication pulses with pulse amplitudes and pulse widths that are likely to cause capture of the heart. In such examples, LCP 402 may then decrease the pulse amplitude and/or pulse width parameters (either individually or simultaneously) until reaching a combination of pulse width and pulse amplitude which does not cause capture of the heart. In general, changing the pulse amplitude and pulse width parameters of the communication pulses changes the energy levels of the communication pulses. Accordingly, changing the energy level of the communication pulses changes the energy delivered to the heart of the patient. It may be that the total energy level of the communication pulses is a large factor in determining whether a communication pulse will capture the heart relative to other factors such as the specific pulse amplitude or specific pulse width.

Figure 12:
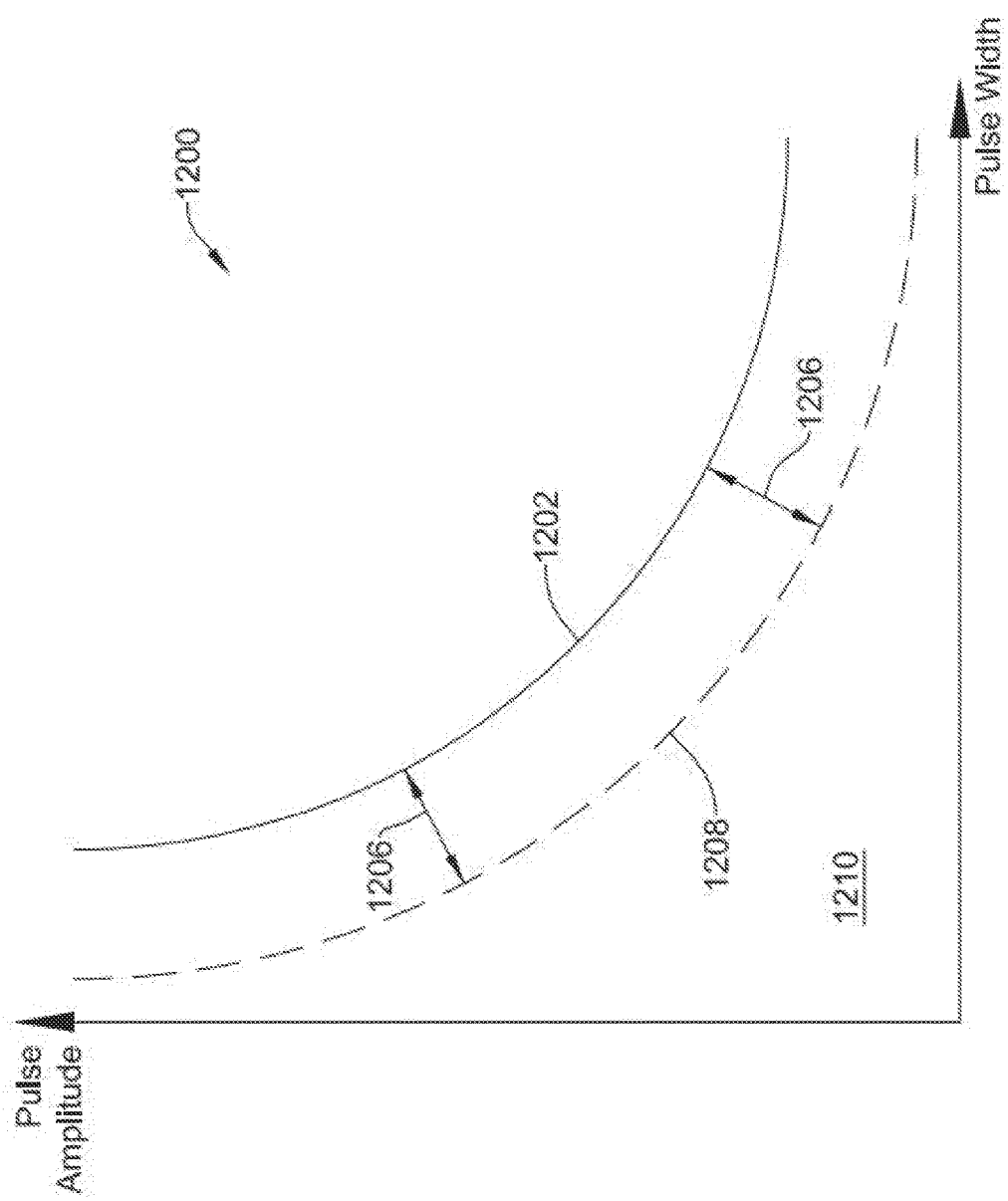
FIG. 12 shows an illustrative graph of pulse amplitude vs. pulse width, in accordance with aspects of the present disclosure.

In at least some examples, LCP 402 may, according to any of the disclosed examples, determine multiple combinations of parameters for conducted communication pulses which result in capture of the heart, thereby determining multiple capture thresholds for the heart. Using the determined multiple combinations of parameters, LCP 402 may further determine a curve or function representative of combinations of parameters which resulted in capture of the heart, for example by using one or more regression techniques. FIG. 12, which is a graph 1200 of pulse amplitude vs. pulse width in voltage and microseconds, includes an illustrative example of what such a curve or function may look like. Curve 1202, then, represents combinations of parameters of conducted communication pulses which resulted in capture of the heart—e.g. curve 1202 may represent a capture threshold curve. Curve 1202 additionally represents a dividing line between combinations of parameters of conducted communication pulses which, when delivered to tissues of a patient, would result in capture of the patient's heart and those that would not result in capture of the patient's heart. For instance, any combinations of pulse amplitudes and pulse widths that lie on curve 1202 or above and to the right of curve 1202 would result in capture. Any combinations of pulse amplitudes and pulse widths that lie below and to the left of curve 1202 would not result in capture. This region is defined as safe zone 1210.

In some examples, LCP 402 may determine a shifted curve related to curve 1202 by a safety margin. The shifted curve is represented by curve 1208. In such examples, safe zone 1210 may be the combinations of pulse amplitudes and pulse widths that lie below and to the left of shifted curve 1208. The amount LCP 402 shifts curve 1202 is represented by safety margin 1206. Safety margin 1206 may represent an amount such that if curve 1202 changes as a function of time or other factors, curve 1202 will not, or is statistically unlikely to, drift below and to the left of curve 1208. LCP 402 may be configured to, under normal communication procedures (such as when communicating according to the first communication mode), not deliver conducted communication pulses with combinations of parameters that lie on curve 1208 or above and to the right of curve 1208.

Regardless of the method that LCP 402 uses to determine that one or more delivered conducted communication pulses have captured the heart of the patient, as discussed above, once LCP 402 determines that one or more delivered conducted communication pulses has captured the heart of the patient, LCP 402 may take one or more actions. In some examples, the first action LCP 402 may take is to determine whether LCP 402 may alter the values of the parameters of the delivered conducted communication pulses to a combination of values which would not cause capture of the patient's heart. In such examples, LCP 402 may determine combinations of parameters which are not expected to cause capture of the heart, for example according to any of the disclosed techniques of FIG. 11. In such examples, LCP 402 may additionally have stored minimum values for combinations of parameters of conducted communication pulses. Such minimum values for combinations of parameters may represent minimum values for the amplitude and/or pulse width of conducted communication pulses that still allow the pulses to be detected by other devices sufficient for communication. In these examples, LCP 402 may compare the values of combinations of parameters which do not cause capture of the heart to the stored minimum values for the combinations of parameters. If there are combinations of values which would not cause capture of the heart and also equal to or greater than the stored minimum values for combinations of parameters, LCP 402 may adjust the values of the amplitude and/or pulse width parameters of conducted communication pulses used during the first communication mode to values that would not cause capture of the heart and are greater than or equal to the minimum values for the parameters. In such examples, LCP 402 may then continue to operate.

In examples where there are no expected combinations of parameters that are greater than or equal to the minimum values for the parameters and would not cause capture of the heart, LCP 402 may switch to a second communication mode, which may be termed a "safe" or "safety" communication mode. Additionally, in at least in some examples, upon detection of one or more delivered communication pulses capturing the heart (for example, after performing any of the protocols detailed with respect to FIGS. 7-11), LCP 402 may skip attempting to determine alternate values for an amplitude and/or pulse width and instead may immediately switch to the second communication mode.

Figure 13:
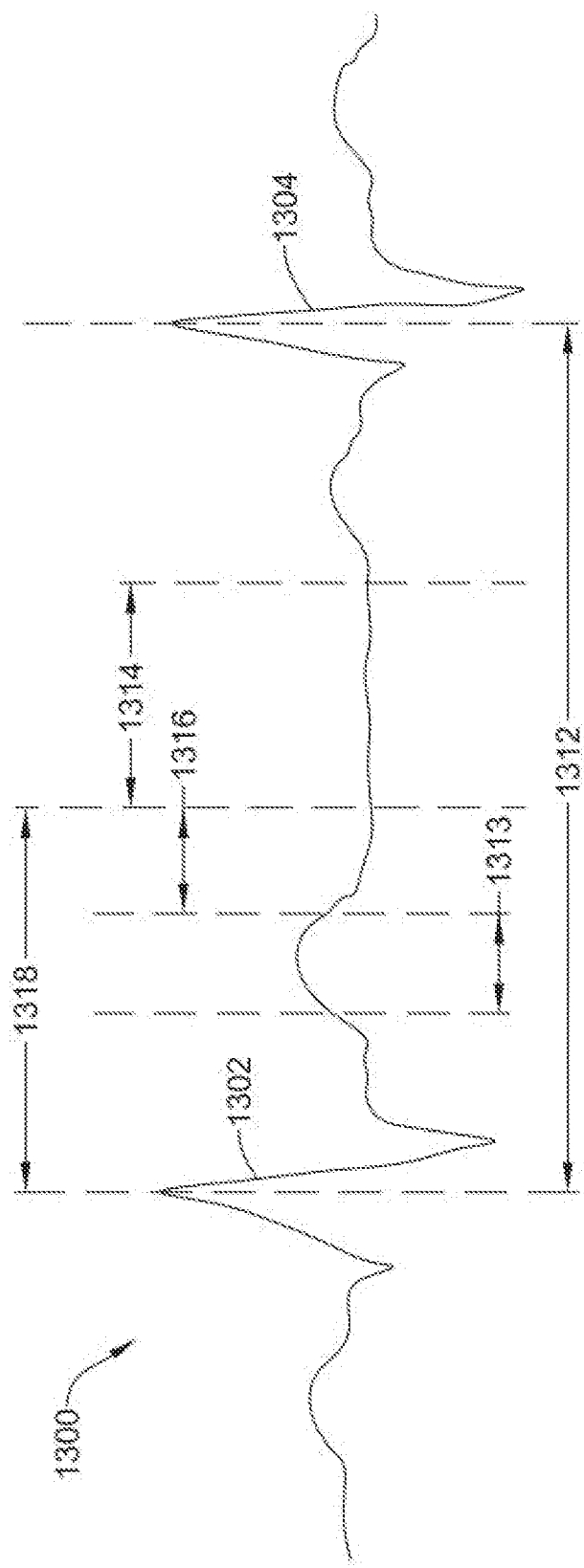
FIG. 13 is a graph of an example cardiac cycle and illustrates when a device may deliver conducted communication pulses, in accordance with an example of the present disclosure.

FIG. 13 depicts an example timing diagram of a normal cardiac cycle and times during the cardiac cycle when a medical device may deliver conducted communication pulses (e.g. bursts) to tissue of a patient when operating in a first example second communication mode. Specifically, FIG. 13 depicts waveform 1300 including a number of different intervals. Two example beats of a heart are depicted with the first beat indicated R-wave 1302 and the second beat indicated by R-wave 1304. A cardiac interval, representing the time between heartbeats is represented by cardiac interval 1312, which spans the time between R-wave 1302 and R-wave 1304. A vulnerable period of the first beat is represented by vulnerable period 1313. According to the first example second communication mode depicted in FIG. 13, LCP 402 may be configured to identify a beat using any of one or more beat detection techniques. LCP 402 may additionally be configured to wait a predetermined amount of time from a feature of an identified beat, such as R-wave 1302 in the first beat of FIG. 13. The predetermined amount of time may generally be long enough to encompass vulnerable period 1313. In the example of FIG. 13, the predetermined amount of time is represented by wait interval 1318. Example values for wait interval 1318 are two-hundred fifty, three-hundred, three-hundred fifty, or four hundred milliseconds, or any other suitable time value.

Additionally or alternatively, in some examples wait interval 1318 may be a function of the heartbeat rate of the patient. For example, LCP 402 may determine a heartbeat rate based on lengths of time between past consecutive beats. In such examples, wait interval 1318 may be a certain percentage of the determined heartbeat period or be determined based on a function including the determined heartbeat rate. In still other examples, LCP 402 may determine a wait interval based off of when the vulnerable period for the identified beat occurs. To determine when the vulnerable period for the first beat of FIG. 13 occurs, LCP 402 may identify the beginning and ending of T-wave 706. Although, in other examples, LCP 402 may use a predictive method for determining the vulnerable period 1313 for the first beat by determining timings for vulnerable periods for preceding beats and applying the determined timings to the first beat. LCP 402 may then determine a wait interval that is ten, twenty-five, or fifty milliseconds long, or any other suitable length of time, after the end of the vulnerable period of the first beat, which is represented by wait interval 1316.

After waiting an amount of time indicated by a wait interval 1316, LCP 402 may allow communication (e.g. communication pulse bursts) during interval period of time, represented by communication interval 1314. Communication interval 1314 may be a second communication interval, contrasting with the first communication interval 614 described with respect to FIG. 6. In some examples, communication interval 1314 may last a predetermined length of time such as fifty, one-hundred, or one-hundred fifty milliseconds, or any other suitable length of time. In general, communication interval 1314 may be shorter than communication interval 614 and may further be short enough to only cause a single capture of the heart if any of the delivered conducted communication pulses during communication interval 1314 do indeed capture the heart. This example communication mode is considered safer because the LCP 402 may only transmit after the vulnerable time and only long enough to cause, at most, one evoked response per communication burst. Thus, even if the communication bursts regularly capture the heart, this mode would results in a safe, albeit, bigeminy rhythm.

As with wait interval 1318, communication interval 1314 may, in some examples, be a function of a determined heartbeat rate. Additionally or alternatively, in some examples, LCP 402 may further determine a timing of when a next beat is expected to occur (for example by determining an estimation interval as detailed in other examples). In such examples, LCP 402 may additionally help ensure that communication interval 1314 ceases at least one-hundred milliseconds (or any other predetermined time) before the time when the next beat is expected to occur.

Figure 14:
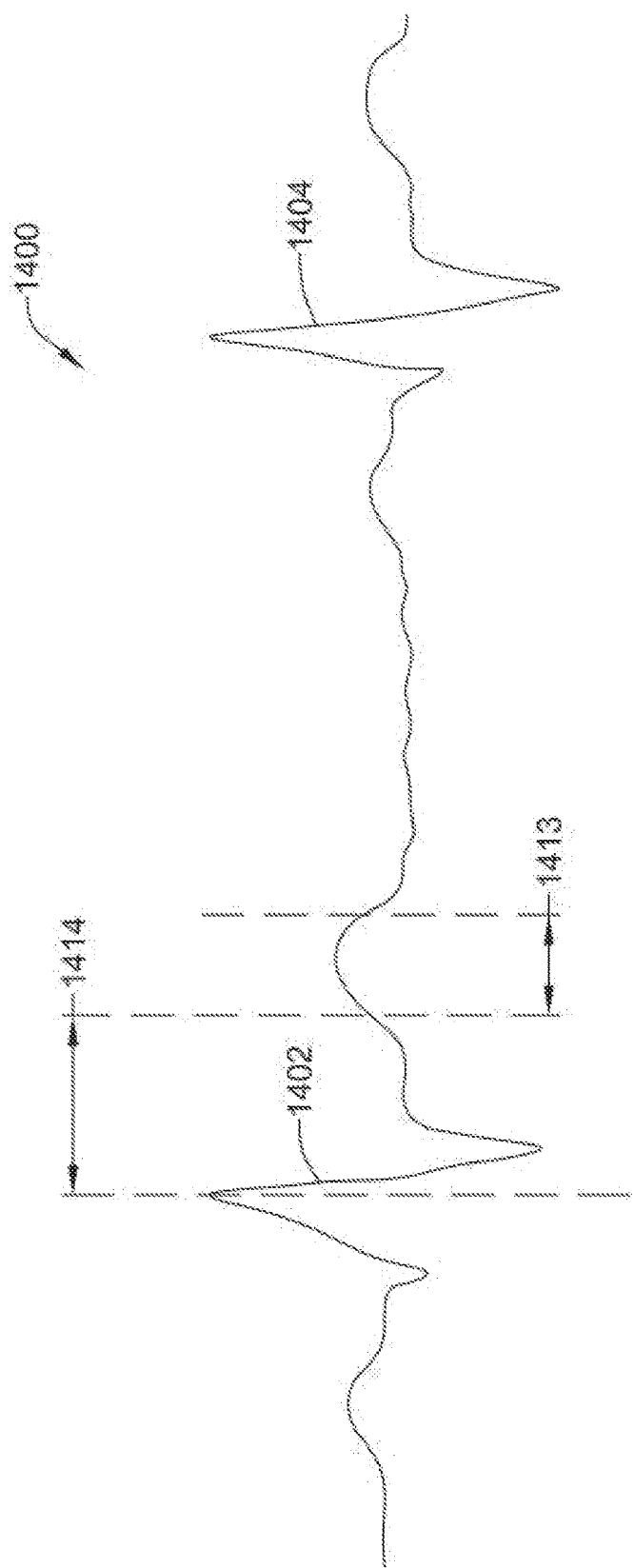
FIG. 14 is a graph of an example cardiac cycle and illustrates when a device may deliver conducted communication pulses, in accordance with an example of the present disclosure.

FIG. 14 depicts another example timing diagram of a normal cardiac cycle and times during the cardiac cycle when a medical device may deliver conducted communication pulses (e.g. communication burst) to tissue of a patient when operating in a second example second communication mode. Specifically, FIG. 14 depicts waveform 1400 including a number of different intervals. Two example beats of a heart are depicted with the first beat indicated R-wave 1402 and the second beat indicated by R-wave 1404. A vulnerable period of the first beat is represented by vulnerable period 1413. According to the example second communication mode of FIG. 14, LCP 402 may be configured to identify a beat using any of one or more beat detection techniques. LCP 402 may additionally communicate only during communication interval 1414, which is another example of a second communication window or period of time. Communication interval 1414 may generally begin immediately after detection of R-wave 1402, during a refractory period of the heart, and last for a predetermined amount of time. Some example values for communication interval 1414 are fifty, one-hundred, and one-hundred fifty milliseconds or any other suitable length of time. However, in other examples, communication interval 1414 may begin a predetermined amount of time after R-wave 1402 such as five, ten, fifteen, or twenty milliseconds, or any other suitable length of time. In at least some examples, communication interval 1414 may have a length of time which helps ensure that communication interval 1414 ends before the beginning of vulnerable period 1413. In other examples, communication interval 1414 may be a variable amount of time. For example, communication interval 1414 may run until the beginning of vulnerable period 1413 instead of for a predetermined amount of time. In such examples, LCP 402 may determine the beginning of vulnerable period 1413 by detecting a rise in the amplitude of sensed cardiac electrical activity above a threshold. This rise in amplitude may coincide with the beginning of the T-wave and be related to the timing of vulnerable period 1413. In other examples, LCP 402 may use a predictive method for determining when vulnerable period 1413 might occur by determining timings for vulnerable periods for preceding beats and applying the determined timings to the identified beat. For example, if LCP 402 had determined that vulnerable periods for the past three beats began an average of two-hundred milliseconds after an R-wave, LCP 402 may estimate that the vulnerable period for the beat identified by R-wave 1402 may begin two-hundred milliseconds after R-wave 1402. Accordingly, LCP 402 may determine an appropriate length of time for communication interval 1414, sometimes with an adequate safety margin.

In yet a third example second communication mode, LCP 402 may switch from another operating mode to a VOO mode of operation. In VOO mode, LCP 402 may take over pacing functions of the heart (if not already the primary device delivering pacing pulses to the heart) and may pace the heart at a regular rhythm. In this example second communication mode, LCP 402 may measure wait intervals and/or communication intervals from the regularly delivered pacing pulses. For example, instead of measuring a wait interval from an R-wave or from the end of a vulnerable period, LCP 402 may measure the wait period from the delivered pacing pulse. Additionally in some examples, LCP 402 may determine that a communication interval begins a certain amount of time from a pacing pulse. This mode may allow for LCP 402 to more easily determine wait intervals and/or communication intervals as LCP 402 may not need to rely on determining morphology features of intrinsic cardiac electrical activity and may queue various intervals off of pacing pulses delivered at regular intervals.

The above described techniques have been described from the perspective of communicating in a first communication mode, detecting capture of heart tissue by communication pulses and transitioning to a second communication mode. Generally, when communicating in the first communication mode, communications may be sent during first communication windows, and when in the second communication mode, communications may be sent during second communication windows where the second communication windows are shorter than the first communication windows. However, techniques of this disclosure also contemplate the reverse. For example, devices communicating in a second communication mode may transition to a first communication mode after determining during one or more capture tests that communication pulses have not captured the heart. In this manner, one or more devices may transition between communication modes based on whether capture tests indicate capture or no capture of heart tissue by communication pulses. Additionally, it should be understood that as described herein, which modes are described as first and second communication modes can be thought of as relative to which mode a device is currently operating in. For example, the first communication mode may always be the communication mode in which a device is currently operating, and the second communication mode may by the communication mode that the device may transition to, based on whether the device determines that a communication pulse captured the heart. For example, in a device is operating in a first communication mode with communication windows which are shorter than communication windows of the second communication mode, the device may transition to the second communication mode after determining that a communication pulse did not capture the heart. Alternatively, in a device is operating in a first communication mode with communication windows which are longer than communication windows of the second communication mode (as in the examples of FIGS. 6-10), the device may transition to the second communication mode after determining that a communication pulse did capture the heart.

The description of the techniques disclosed herein should not be viewed as limiting in any manner. Variations on the described example devices and techniques are within the scope of this disclosure. For example, although the intervals of multiple techniques have generally been described as being measured from an R-wave of a QRS complex, in other examples, the intervals may be measured from other features of sensed electrical activity. For instance, in examples that include paced beats, the wait, communication, and/or other intervals may all be determined based on the timing of the delivered pacing pulse. In still other examples, the intervals may be determined based off of each other. As one example, a wait interval may be determined off of the timing of an intrinsic feature of sensed electrical activity, such as an R-wave. Then, a communication interval or a sense interval may be determined based off of the end of the wait interval. In still other examples, different intervals may be determined based on different features. For instance, the wait interval may be determined based off of the timing of an R-wave, while the communication interval may be determined based off of the timing of the end of the vulnerable period. These are just a few examples. It should be understood that the techniques disclosed herein encompass all examples where any interval is determined based off of a timing of any feature of the sensed electrical activity or another interval.

Additionally, although the techniques disclosed herein were described with a single device delivering conducted communication pulses, sensing electrical activity, and determining intervals, parameters, and other features, in other examples such operations may be distributed between multiple devices. For instance, in other examples, LCP 402 may be configured to only deliver conducted communication pulses (and possibly pacing pulses) at specific times or at the expiration of specific intervals. Another device may be responsible for sensing electrical activity, determining parameter values, intervals lengths, and/or other features and communicating such information to LCP 402. As one illustrative example, another device may determine that conducted communication pulses delivered by LCP 402 are capturing the heart. The other device may then communicate a command to LCP 402 to perform one or more of the methods described with respect to FIGS. 7-11. Within the one or more methods, the other device may determine the interval values, the amplitude and/or pulse width values, and/or other values and communicate the values to LCP 402. The other device may additionally sense for cardiac electrical activity during any sense intervals or for a next beat around the end of an estimation interval. LCP 402 may then simply deliver conducted communication pulses with the indicated amplitude and pulse width parameters at the indicated times or at the end of the indicated intervals. Alternatively, instead of communicating the various values to LCP 402, the other device may simply send a communication to LCP 402 commanding LCP 402 to deliver a conducted communication pulse (and possibly specific amplitude and/or pulse width values) to tissues of the patient at an appropriate time, with the other device tracking the various intervals. Accordingly, the techniques disclosed herein may not rely on a specific apportionment of tasks between one or more devices. As such, the disclosed techniques should be interpreted to encompass all implementations of the techniques whereby specific tasks are split between multiple devices.

Figure 15:
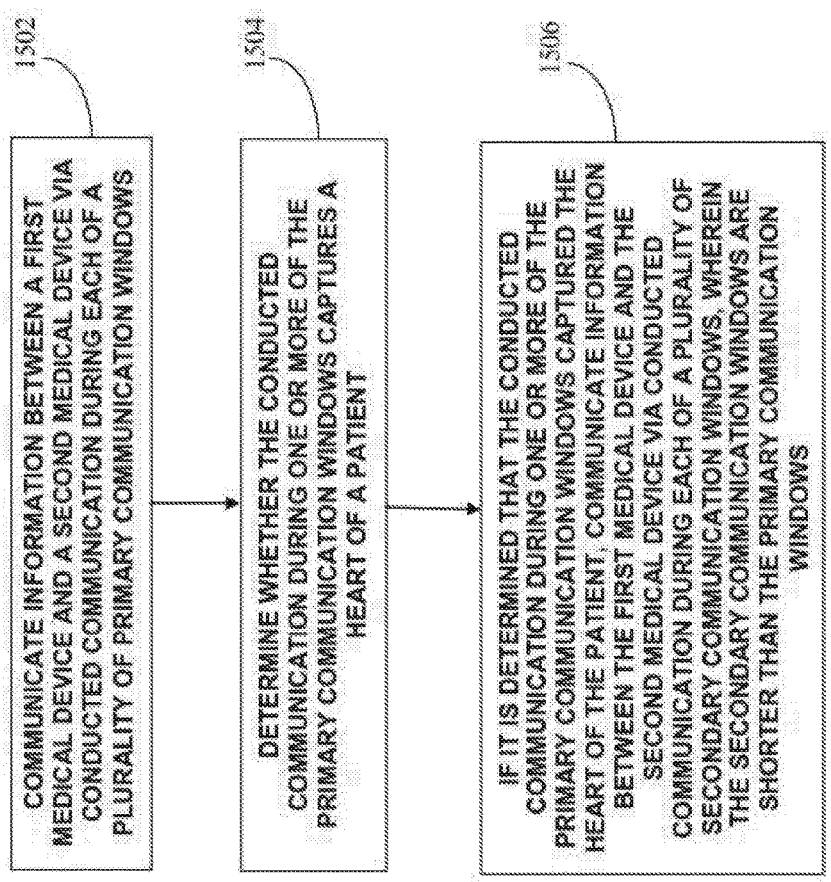
FIG. 15 is a flow diagram of an illustrative method that may be implemented by a medical device or medical device system, such as the illustrative medical devices and medical device systems described with respect to FIGS. 1-5.

FIG. 15 is a flow diagram of an illustrative method that may be implemented by an implantable medical device, such as shown in FIGS. 1-2, or a medical device system such as shown in FIGS. 4-5. Although the method of FIG. 15 will be described with respect to LCP 100 and MD 200, the illustrative method of FIG. 15 may be performed using any suitable medical device or medical device system.

According to the method depicted in FIG. 15, a first medical device, such as MD 200, may be implanted within a patient, such as if MD 200 is an ICP, an ICD, an S-ICD, or may be disposed in proximity to the patient, such as if MD 200 is an external medical device. MD 200 may be part of a medical device system along with a second medical device, such as LCP 100. In such a medical device system, MD 200 and LCP 100 may communicate information between the devices via conducted communication during each of a plurality of first communication windows, as shown at 1502. At least one of MD 200 and LCP 100 may determine whether the conducted communication during one or more of the first communication windows captures a heart of a patient, as shown at 1504. If either of MD 200 or LCP 100 determines that the conducted communication during one or more of the first communication windows captured the heart of the patient, MD 200 and LCP 100 may then communicate information between the devices via conducted communication during each of a plurality of second communication windows, wherein the second communication windows are shorter than the first communication windows, as shown at 1506.

FIG. 16 is a flow diagram of an illustrative method that may be implemented by an implantable medical device, such as shown in FIGS. 1-2, or a medical device system such as shown in FIGS. 4-5. Although the method of FIG. 16 will be described with respect to LCP 100 and MD 200, the illustrative method of FIG. 16 may be performed using any suitable medical device or medical device system.

According to the method depicted in FIG. 16, a first medical device, such as MD 200, may be implanted within a patient, such as if MD 200 is an ICP, an ICD, an S-ICD, or may be disposed in proximity to the patient, such as if MD 200 is an external medical device. MD 200 may be part of a medical device system along with a second medical device, such as LCP 100. In such a medical device system, MD 200 and LCP 100 may communicate information between the devices via conducted communication using communication pulses having a first energy level, as shown at 1602. One or more of MD 200 and LCP 100 may then perform a capture threshold test to identify a capture threshold for the communication pulses, as shown at 1604. MD 200 and LCP 100 may then change the energy level of the communication pulses from the first energy level to a second energy level, the second energy level based on the capture threshold identified during the capture threshold test, as shown at 1606. MD 200 and LCP 100 may then communicate information between the devices via conducted communication using communication pulses having the second energy level, as shown at 1608.

Those skilled in the art will recognize that the present disclosure may be manifested in a variety of forms other than the specific examples described and contemplated herein. For instance, as described herein, various examples include one or more modules described as performing various functions. However, other examples may include additional modules that split the described functions up over more modules than that described herein. Additionally, other examples may consolidate the described functions into fewer modules. Accordingly, departure in form and detail may be made without departing from the scope and spirit of the present disclosure as described in the appended claims.

What is claimed is:

1. A method of communicating information between a plurality of medical devices in a medical device system, wherein at least one of the medical devices is an implantable medical device for implantation in a patient, the method comprising:

communicating information between a first medical device and a second medical device via conducted communication using communication pulses having a first energy level;

performing a capture threshold test to identify a capture threshold for the communication pulses;

changing the energy level of the communication pulses from the first energy level to a second energy level, wherein the second energy level is based on the capture threshold identified during the capture threshold test; and communicating information between the first medical device and the second medical device via conducted communication using communication pulses having the second energy level.

2. The method of claim 1, wherein the first energy level is represented by a first pulse amplitude and a first pulse width, and the second energy level is represented by the first pulse amplitude and a second pulse width, wherein the second pulse width is different from the first pulse width.

3. The method of claim 1, wherein the first energy level is represented by a first pulse amplitude and a first pulse width, and the second energy level is represented by a second pulse amplitude and the first pulse width, wherein the second pulse amplitude is different from the first pulse amplitude.

4. The method of claim 1, wherein the first energy level is represented by a first pulse amplitude and a first pulse width, and the second energy level is represented by a second pulse amplitude and a second pulse width, wherein the second pulse width is different from the first pulse width and the second pulse amplitude is different from the first pulse amplitude.

5. The method of claim 1, wherein performing the capture threshold test comprises:
delivering one or more communication pulses at a capture threshold test energy level;
determining if the one or more communication pulses at the capture threshold test energy level captured the heart of the patient, and:
if so, identifying a capture threshold based, at least in part, on the capture threshold test energy level; and
if not, changing the capture threshold test energy level and returning to the delivering step.

6. The method of claim 5, wherein changing the capture threshold test energy level comprises increasing the capture threshold test energy level.

7. The method of claim 1, wherein performing the capture threshold test comprises:
delivering one or more communication pulses at a capture threshold test energy level;
determining if the one or more communication pulses at the capture threshold test energy level captured the heart of the patient, and:
if so, changing the capture threshold test energy level and returning to the delivering step; and
if not, identifying a capture threshold based, at least in part, on the capture threshold test energy level.

8. The method of claim 7, wherein changing the capture threshold test energy level comprises decreasing the capture threshold test energy level.

9. The method of claim 1, wherein performing the capture threshold test comprises incrementally increases the energy level of the communication pulses until the communication pulses capture the heart of the patient, and then sets the second energy level at a margin below the energy level that captured the heart.

10. The method of claim 1, wherein performing the capture threshold test comprises incrementally decreases the energy level of the communication pulses until the communication pulses no longer capture the heart of the patient, and then sets the second energy level at a margin below the energy level that no longer captured the heart.

11. The method of claim 1, wherein the capture threshold test is performed from time to time, and the energy level of the communication pulses used for communicating information between the first medical device and the second medical device is updated accordingly from time to time.

12. An implantable medical device configured to communicate information to a remote medical device via conducted communication using communication pulses applied via two or more electrodes, the implantable medical device comprising:
a housing;
a controller housed by the housing;
the controller configured to:
communicate information to the remote medical device via conducted communication using communication pulses having a first energy level applied via the two or more electrodes;
perform a capture threshold test to identify a capture threshold for the communication pulses;
change the energy level of the communication pulses from the first energy level to a second energy level, wherein the second energy level is based on the capture threshold identified during the capture threshold test; and
subsequently communicate information to the remote medical device via conducted communication using communication pulses having the second energy level.

13. The implantable medical device of claim 12, wherein the controller is configured to perform the capture threshold test by:
delivering one or more communication pulses at a capture threshold test energy level;
determining if the one or more communication pulses at the capture threshold test energy level captured the heart of the patient, and:
if so, identifying a capture threshold based, at least in part, on the capture threshold test energy level; and
if not, changing the capture threshold test energy level and delivering one or more communication pulses at the changed capture threshold test energy level and determining if the one or more communication pulses at the changed capture threshold test energy level captured the heart of the patient.

14. The implantable medical device of claim 13, wherein changing the capture threshold test energy level comprises increasing the capture threshold test energy level.

15. The implantable medical device of claim 12, wherein the controller is configured to perform the capture threshold test by:
delivering one or more communication pulses at a capture threshold test energy level;
determining if the one or more communication pulses at the capture threshold test energy level captured the heart of the patient, and:
if so, changing the capture threshold test energy level and returning to the delivering step; and
if not, identifying a capture threshold based, at least in part, on the capture threshold test energy level.

16. The implantable medical device of claim 15, wherein changing the capture threshold test energy level comprises decreasing the capture threshold test energy level.

17. The implantable medical device of claim 12, wherein performing the capture threshold test comprises incrementally increases the energy level of the communication pulses until the communication pulses capture the heart of the patient, and then sets the second energy level a margin below the energy level that captured the heart.

18. The implantable medical device of claim 12, wherein performing the capture threshold test comprises incrementally decreases the energy level of the communication pulses until the communication pulses no longer capture the heart of the patient, and then sets the second energy level a margin below the energy level that no longer captured the heart.

19. An implantable medical device for implantation in a patient, comprising:
- a housing;
- a plurality of electrodes exposed outside of the housing;
- a communication module for delivering conducted communication pulses via two or more of the plurality of electrodes;
- a sensing module for sensing cardiac activity of a heart of the patient;
- a controller operatively coupled to the communication module and the sensing module, the controller is configured to instruct the communication module to deliver conducted communication pulses having different energy levels, to identify via the sensing module which of the conducted communication pulses result in capture of a patient's heart, and to identify a capture threshold energy level for the conducted communication pulses; and
- the controller is further configured to instruct the communication module to subsequently deliver conducted communication pulses that have an energy level that is below the capture threshold energy level by a capture threshold margin in order to communicate information from the implantable medical device to another device.

20. The implantable medical device of claim 19, wherein the controller is configured to repeat from time to time:
- instructing the communication module to deliver conducted communication pulses having different energy levels, to identify via the sensing module which of the conducted communication pulses result in capture of a patient's heart, and to identify a capture threshold energy level for the conducted communication pulses; and
- instructing the communication module to subsequently deliver conducted communication pulses that have an energy level that is below the capture threshold energy level by a capture threshold margin in order to communicate information from the implantable medical device to another device.

* * * * *